United States Patent
Hirokawa

(10) Patent No.: US 11,900,533 B2
(45) Date of Patent: Feb. 13, 2024

(54) OPHTHALMIC SYSTEM, IMAGE SIGNAL OUTPUT METHOD, IMAGE SIGNAL OUTPUT DEVICE, PROGRAM, AND THREE-DIMENSIONAL FUNDUS IMAGE GENERATION METHOD

(71) Applicant: NIKON CORPORATION, Tokyo (JP)

(72) Inventor: Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 56 days.

(21) Appl. No.: 16/753,149

(22) PCT Filed: Oct. 11, 2018

(86) PCT No.: PCT/JP2018/037998
§ 371 (c)(1),
(2) Date: Apr. 2, 2020

(87) PCT Pub. No.: WO2019/074077
PCT Pub. Date: Apr. 18, 2019

(65) Prior Publication Data
US 2020/0258295 A1    Aug. 13, 2020

(30) Foreign Application Priority Data
Oct. 13, 2017  (JP) ................. 2017-199485

(51) Int. Cl.
*A61B 3/00* (2006.01)
*G06T 17/00* (2006.01)
*G06T 7/33* (2017.01)
*A61B 3/10* (2006.01)
*A61B 3/12* (2006.01)
*A61B 5/055* (2006.01)
*G06F 3/0482* (2013.01)
*G06T 19/20* (2011.01)

(52) U.S. Cl.
CPC ............ *G06T 17/00* (2013.01); *A61B 3/0025* (2013.01); *A61B 3/0041* (2013.01); *A61B 3/1005* (2013.01); *A61B 3/12* (2013.01); *A61B 5/055* (2013.01); *G06F 3/0482* (2013.01); *G06T 7/33* (2017.01); *G06T 19/20* (2013.01);
(Continued)

(58) Field of Classification Search
None
See application file for complete search history.

(56) References Cited

U.S. PATENT DOCUMENTS

| 7,219,997 B2 | 5/2007 | Yokota |
| 9,649,031 B2 | 5/2017 | Hemert |

(Continued)

FOREIGN PATENT DOCUMENTS

| JP | 2000-210260 A | 8/2000 |

OTHER PUBLICATIONS

Han et al. (Three Dimensional Simulation for Blood Vessel of Ocular Fundus, IEEE, 2009) (Year: 2009).*

(Continued)

*Primary Examiner* — Kyle Zhai
(74) *Attorney, Agent, or Firm* — Foley & Lardner LLP

(57) ABSTRACT

An image signal output method including outputting a first image signal to display an eyeball model selection screen for selecting one eyeball model from out of plural eyeball models of different types, converting a two-dimensional fundus image of the subject eye so as to generate a three-dimensional fundus image based on a selected eyeball model, and outputting a second image signal to display a fundus image display screen including the three-dimensional fundus image.

8 Claims, 23 Drawing Sheets

(52) U.S. Cl.
CPC .......................... *G06F 2203/04803* (2013.01); *G06T 2200/24* (2013.01); *G06T 2207/10088* (2013.01); *G06T 2207/30041* (2013.01); *G06T 2210/41* (2013.01); *G06T 2219/2004* (2013.01)

(56) References Cited

U.S. PATENT DOCUMENTS

| | | | |
|---|---|---|---|
| 2012/0002164 A1* | 1/2012 | Yamamoto | A61B 3/1025 351/206 |
| 2012/0189184 A1* | 7/2012 | Matsumoto | A61B 3/102 382/131 |
| 2012/0320339 A1* | 12/2012 | Yonezawa | A61B 3/102 351/208 |
| 2013/0211284 A1* | 8/2013 | Berry | A61B 3/02 600/558 |

OTHER PUBLICATIONS

Zanet et al., "Landmark Detection for Fusion of Fundus and MRI Toward a Patient-Specific Multimodal Eye Model", IEEE Transactions on Biomedical Engineering, vol. 62, No. 2, 2015, pp. 532-540.
Office Action issued in corresponding Japanese Patent Application No. 2019-548246, dated Jun. 14, 2022, with English translation, 8 pages.

\* cited by examiner

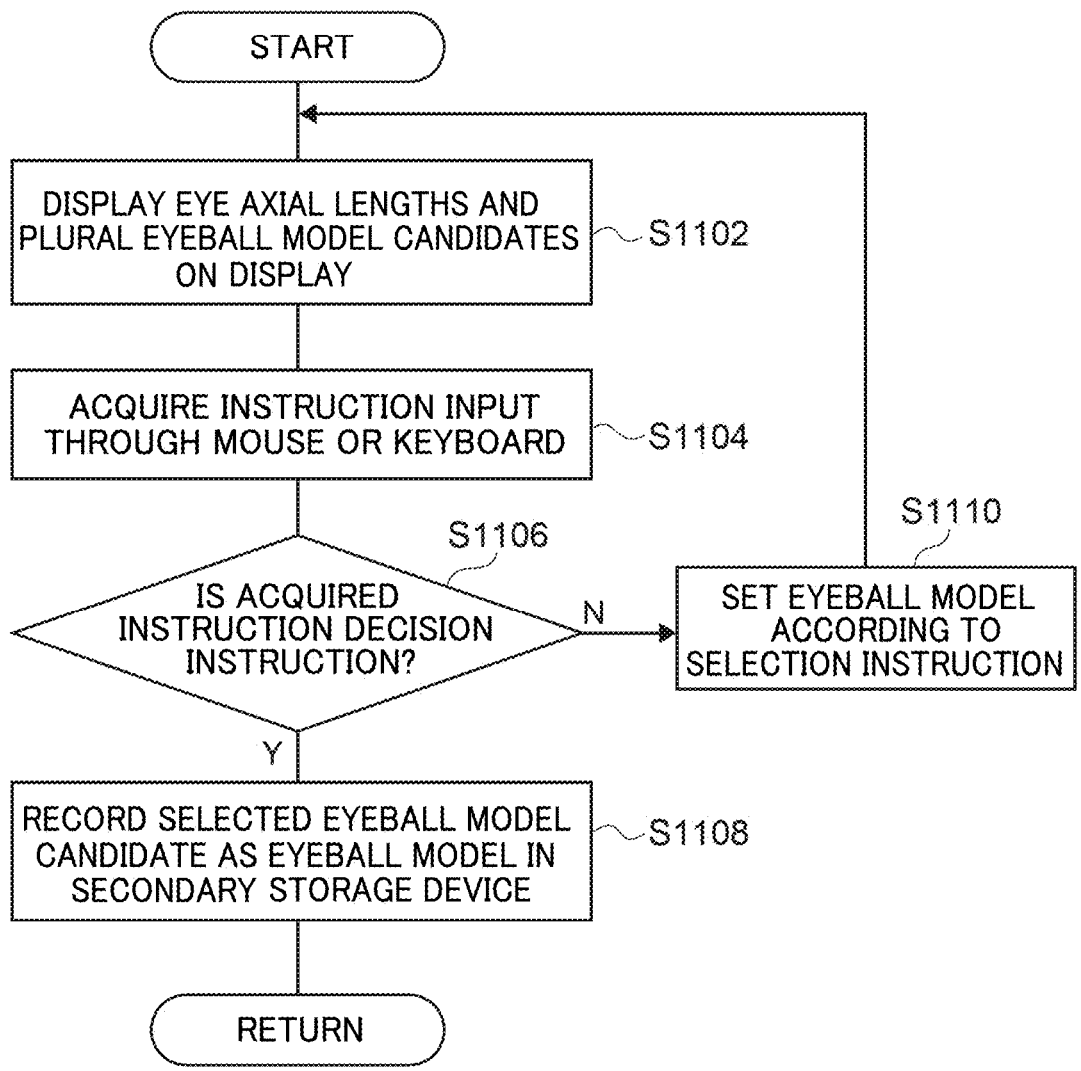

FOVEA CENTRALIS OPTIC NERVE HEAD POSITION

FOVEA CENTRALIS OPTIC NERVE HEAD POSITION

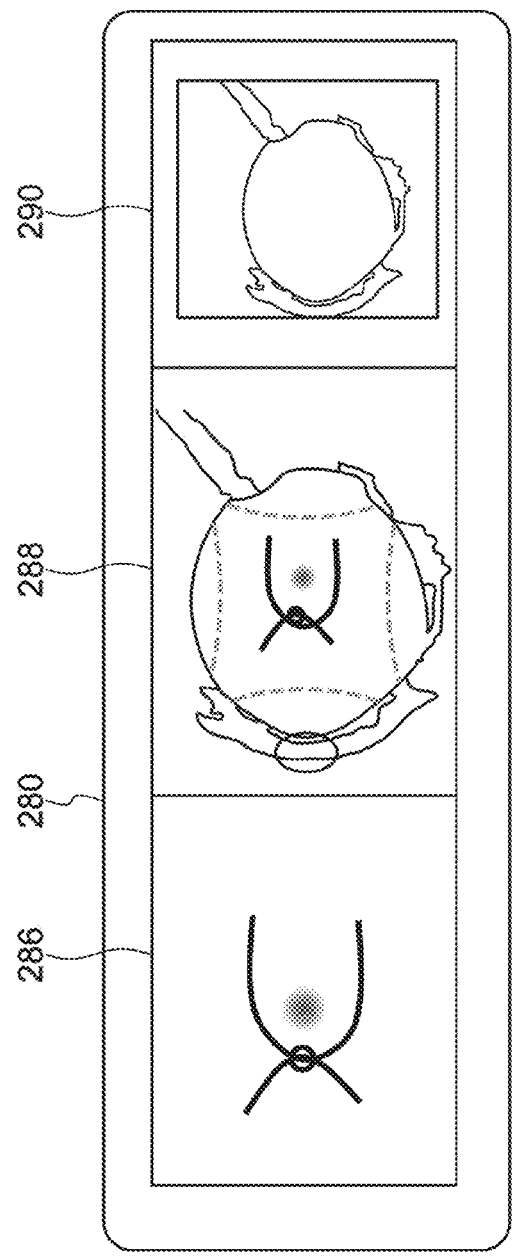

OPHTHALMIC SYSTEM, IMAGE SIGNAL OUTPUT METHOD, IMAGE SIGNAL OUTPUT DEVICE, PROGRAM, AND THREE-DIMENSIONAL FUNDUS IMAGE GENERATION METHOD

TECHNICAL FIELD

The present disclosure relates to an ophthalmic system, an image signal output method, an image signal output device, a program, and a three-dimensional fundus image generation method.

BACKGROUND ART

Technology used to generate a three-dimensional image of a fundus from plural two-dimensional images of the fundus is known. For example, Japanese Patent Application Laid-Open (JP-A) No. 2004-24739 discloses technology in which even in cases in which an eyeball has deformed from being completely spherical, an eyeball template is created as a three-dimensional eyeball model, and plural two-dimensional images are wrapped around the eyeball template to generate a three-dimensional image of the fundus which is displayed on a display. Specifically, in JP-A No. 2004-24739, the size of the eyeball (depth from the surface of the cornea to the fundus) and the curvature of the fundus are measured, and the eyeball template is created based on these measurement values.

SUMMARY OF INVENTION

A first aspect of the present disclosure is an image signal output method including outputting a first image signal to display an eyeball model selection screen for selecting one eyeball model from out of plural eyeball models of different types, converting a two-dimensional fundus image of a subject eye so as to generate a three-dimensional fundus image based on a selected eyeball model, and outputting a second image signal to display a fundus image display screen including the three-dimensional fundus image.

A second aspect of the present disclosure is an image signal output device including a first output section configured to output a first image signal to display an eyeball model selection screen for selecting one eyeball model from out of plural eyeball models of different types, a generation section configured to convert a two-dimensional fundus image so as to generate a three-dimensional fundus image based on a selected eyeball model, and a second output section configured to output a second image signal to display a fundus image display screen including the three-dimensional fundus image.

A third aspect of the present disclosure is an image signal output device including a first image generation section configured to generate an eyeball model selection screen for selecting one eyeball model from out of plural eyeball models of different types, a three-dimensional image generation section configured to convert a two-dimensional fundus image so as to generate a three-dimensional fundus image based on a selected eyeball model, a second image generation section configured to generate a fundus image display screen including the three-dimensional fundus image, and an image signal output section configured to output an image signal corresponding to the eyeball model selection screen or the fundus image display screen.

A fourth aspect of the present disclosure is a program to cause a computer to execute processing including outputting a first image signal to display an eyeball model selection screen for selecting one eyeball model from out of plural eyeball models of different types, converting a two-dimensional fundus image so as to generate a three-dimensional fundus image based on a selected eyeball model, and outputting a second image signal to display a fundus image display screen including the three-dimensional fundus image.

A fifth aspect of the present disclosure is a program to cause a computer to execute processing including generating an eyeball model selection screen for selecting one eyeball model from out of plural eyeball models of different types, converting a two-dimensional fundus image so as to generate a three-dimensional fundus image based on a selected eyeball model, generating a fundus image display screen including the three-dimensional fundus image, and outputting an image signal corresponding to the eyeball model selection screen or the fundus image display screen.

A sixth aspect of the present disclosure is an ophthalmic system including an ophthalmic imaging device and an image signal output device. The image signal output device is configured to execute processing including outputting a first image signal to display an eyeball model selection screen for selecting one eyeball model from out of plural eyeball models of different types, converting a two-dimensional fundus image obtained by imaging using the ophthalmic imaging device so as to generate a three-dimensional fundus image based on a selected eyeball model, and outputting a second image signal to display a fundus image display screen including the three-dimensional fundus image.

A seventh aspect of the present disclosure is a three-dimensional fundus image generation method including generating an eyeball model of a subject eye based on eyeball shape information for the subject eye, performing positional alignment of a two-dimensional fundus image of the subject eye and the eyeball model based on plural biological feature points in the two-dimensional fundus image and positions of the plural biological feature points in the eyeball model, and converting the two-dimensional fundus image so as to generate a three-dimensional fundus image based on the position alignment.

An eighth aspect of the present disclosure is an ophthalmic system including an MRI device and an image generation device. The image generation device is configured to execute processing including generating an eyeball model of a subject eye based on eyeball shape information of the subject eye using three-dimensional information obtained by the MRI device, performing positional alignment of a two-dimensional fundus image of the subject eye obtained by imaging using an ophthalmic imaging device and the eyeball model based on plural biological feature points in the two-dimensional fundus image and positions of the plural biological feature points in the eyeball model, and converting the two-dimensional fundus image so as to generate a three-dimensional fundus image based on the position alignment.

BRIEF DESCRIPTION OF DRAWINGS

FIG. 8A illustrates a fixation position when an axis of vision of a subject eye is aligned with an axis of measurement light from an eye axial length measurement device. FIG. 8B illustrates a fixation position when an LCD is positioned further along an X positive direction than the fixation position. FIG. 8C illustrates a fixation position when an LCD is positioned further along an X negative direction than the fixation position.

FIG. 11 is a flowchart illustrating contents of an eyeball model generation sub-routine according to the first exemplary embodiment.

FIG. 25 is a diagram illustrating an example of a fundus image display screen according to the second exemplary embodiment.

DESCRIPTION OF EMBODIMENTS

Detailed explanation follows regarding exemplary embodiments of the present disclosure, with reference to the drawings.

First Exemplary Embodiment

System Overview

Figure 1:
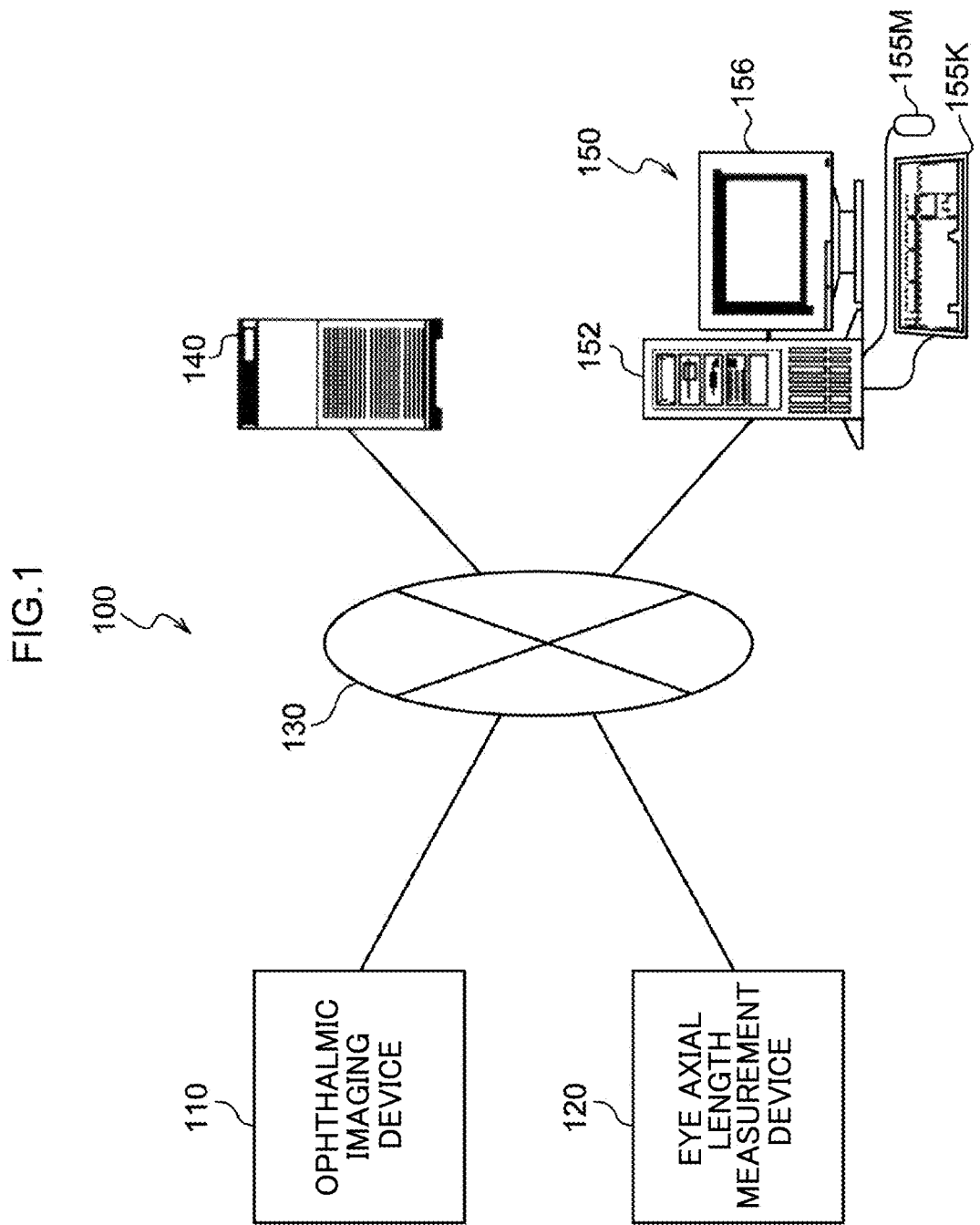
FIG. 1 is a diagram illustrating an example of a schematic configuration of a fundus image display system according to a first exemplary embodiment of the present disclosure.

Explanation follows regarding configuration of a fundus image display system 100, with reference to FIG. 1. As illustrated in FIG. 1, the fundus image display system 100 includes an ophthalmic imaging device 110 that captures a fundus image of a subject eye, an eye axial length measurement device 120 that measures an eye axial length of the subject eye, an image management server 140 that stores fundus image data received from the ophthalmic imaging device 110 and eye axial length data received from the eye axial length measurement device 120, and an image viewer 150 that displays fundus images and eye axial lengths acquired from the image management server 140. The ophthalmic imaging device 110, the eye axial length measurement device 120, the image management server 140, and the image viewer 150 are connected together through a network 130. Note that the image viewer 150 is an example of an image signal output device of the present disclosure. The image management server 140 is an example of an image signal output device or an image generation device of the present disclosure.

Figure 2:
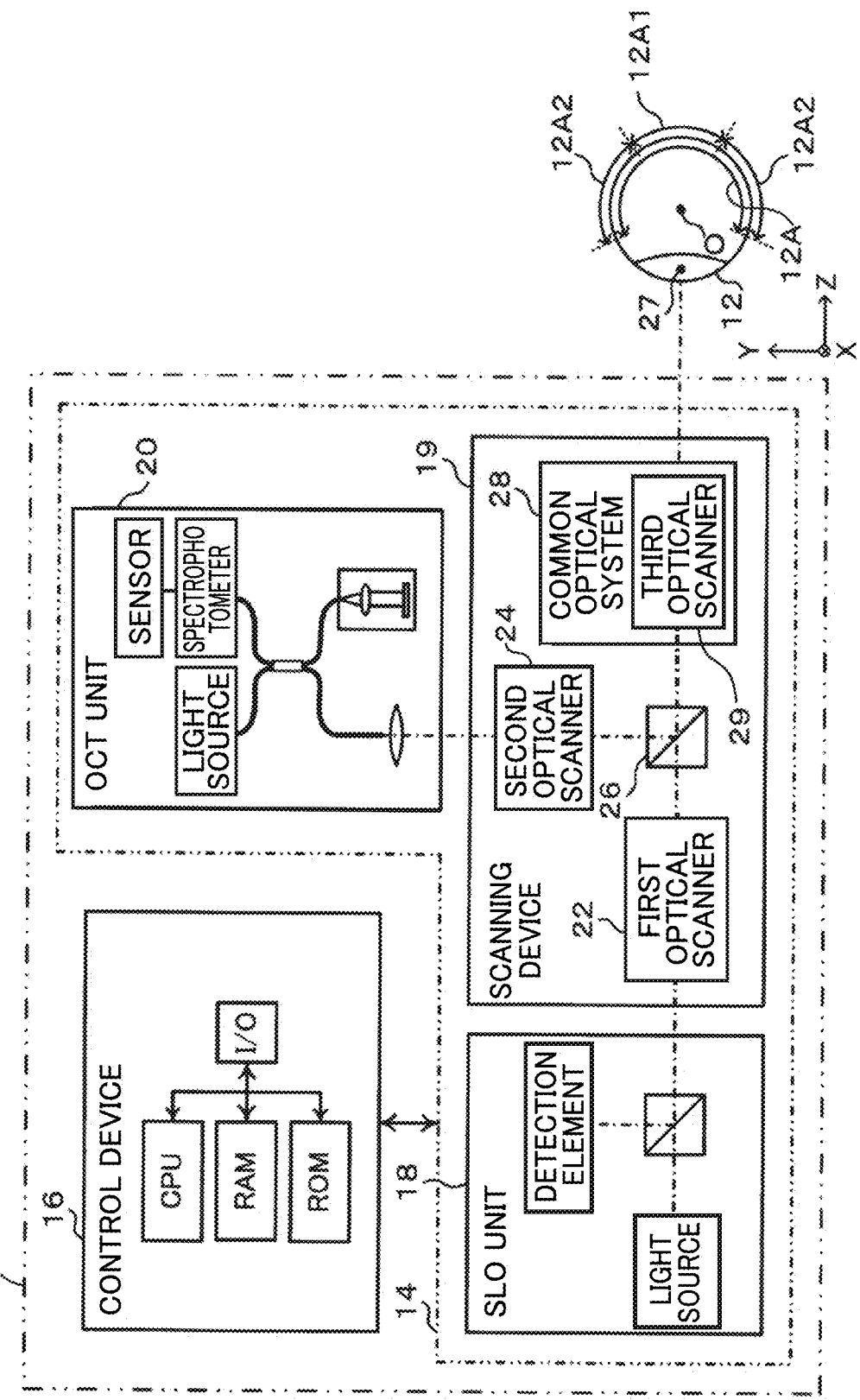
FIG. 2 is a diagram illustrating an example of an overall configuration of an ophthalmic imaging device according to the first exemplary embodiment.

Explanation follows regarding an example of configuration of the ophthalmic imaging device 110, with reference to FIG. 2. As illustrated in FIG. 2, the ophthalmic imaging device 110 includes a device body 14 that images the fundus of the subject eye, and a control device 16. The control device 16 is configured by a computer including a CPU, RAM, ROM, and an input/output (I/O) port, and is connected to the network 130 through a non-illustrated communication interface (I/F). Although the example given here employs a single CPU, the technology disclosed herein is not limited thereto, and plural CPUs may be applied. In the following explanation, "imaging" refers to the acquisition by a user of an image representing an imaging subject using the ophthalmic imaging device 110, and is also referred to as "image capture" on occasion. The device body 14 operates under the control of the control device 16. The device body 14 includes an SLO unit 18, a scanning device 19, and an OCT unit 20.

The scanning device 19 includes a first optical scanner 22, a second optical scanner 24, a dichroic mirror 26, and a common optical system 28 including a third optical scanner 29.

In the following explanation, when the ophthalmic imaging device 110 is installed on a horizontal plane, the horizontal direction is referred to as the "X direction", a direction perpendicular to the horizontal direction is referred to as the "Y direction", and a direction from the anterior segment toward the fundus of a subject eye 12 so as to pass through an eyeball center O is referred to as the "Z direction". Accordingly, the X direction is a direction perpendicular to both the Y direction and the Z direction.

The ophthalmic imaging device 110 according to the first exemplary embodiment includes two functions as examples of main functions that can be implemented by the ophthalmic imaging device 110. The first function is a function in which the ophthalmic imaging device 110 operates as a scanning laser ophthalmoscope (hereafter SLO) to perform SLO imaging (this function is referred to hereafter as the SLO imaging system function). The second function is a function in which the ophthalmic imaging device 110 operates as an optical coherence tomography (hereafter OCT) device to perform OCT imaging (this function is referred to hereafter as the OCT imaging system function).

The SLO imaging system function is implemented by the control device 16, the SLO unit 18, and the scanning device 19 that includes the first optical scanner 22 out of the configuration of the ophthalmic imaging device 110. The SLO unit 18 includes a light source, a detection element, and the like, and is configured to perform image capture of the fundus of the subject eye 12. Namely, the ophthalmic imaging device 110 operates in the SLO imaging system function to perform image capture in which the fundus (for example an imageable region 12A) of the subject eye 12 serves as an imaging subject. Specifically, light from the SLO unit 18 (referred to hereafter as SLO light) is passed through the pupil of the subject eye 12 (specifically, through a pupil center point 27, described later) and onto the imageable region 12A by the scanning device 19 while being scanned in the X direction (horizontal direction) by the first optical scanner 22 and being scanned in the Y direction (vertical direction) by the third optical scanner 29, and a fundus image configured by reflected light is acquired by the SLO unit 18. Note that since the SLO imaging system function is a known function, detailed explanation thereof is omitted.

The OCT imaging system function is implemented by the control device 16, the OCT unit 20, and the scanning device 19 that includes the second optical scanner 24. The OCT unit 20 includes a light source, a spectrophotometer, a sensor, a reference optical system, and the like, and is configured to capture images of plural tomographic regions in a fundus layer thickness direction. Namely, the ophthalmic imaging device 110 operates in the OCT imaging system function to capture images of tomographic regions that are regions in the fundus layer thickness direction (for example the imageable region 12A). Specifically, light from the OCT unit 20 (referred to hereafter as measurement light) is passed through the pupil of the subject eye 12 and onto the imageable region 12A by the scanning device 19 while being scanned in the X direction (horizontal direction) by the second optical scanner 24 and being scanned in the Y direction (vertical direction) by the third optical scanner 29). Light reflected from the measurement light interferes with reference light to generate interference light. The OCT unit 20 detects respective spectral components of the interference light, and the control device 16 employs the detection results thereof to acquire physical quantities (for example a tomographic image) representing the tomographic regions. Note that since the OCT imaging system function is a known function, detailed explanation thereof is omitted.

In the following explanation, the SLO light and the measurement light are both light scanned in two dimensions, namely in the X direction and the Y direction. Accordingly, where it is not necessary to distinguish between the SLO light and the measurement light in the explanation, the SLO light and the measurement light are referred to collectively as scanning light.

Note that in the first exemplary embodiment, the ophthalmic imaging device 110 including functionality that employs scanning light is described as an example. However, there is no limitation to ophthalmic imaging devices including functionality that employs scanning light, and any functionality enabling observation of the subject eye 12 may be adopted. For example, there is no limitation to shining scanning light, and application may be made to any ophthalmic imaging device including functionality that enables observation of the fundus of the subject eye 12 by shining light toward the fundus of the subject eye 12. Namely, there is no limitation to employing light reflected from the subject eye 12 when scanned with scanning light, and functionality to observe the subject eye 12 simply by shining light is also acceptable. There is, moreover, no limitation to shining light into the subject eye 12. For example, functionality to observe the subject eye 12 using light such as fluorescent light generated in the subject eye 12 is also acceptable. Accordingly, light employed when observing the subject eye 12 is a concept encompassing both light reflected from the fundus and light generated at the fundus. This concept is referred to as "light from the subject eye 12" in the following explanation.

Figure 3:
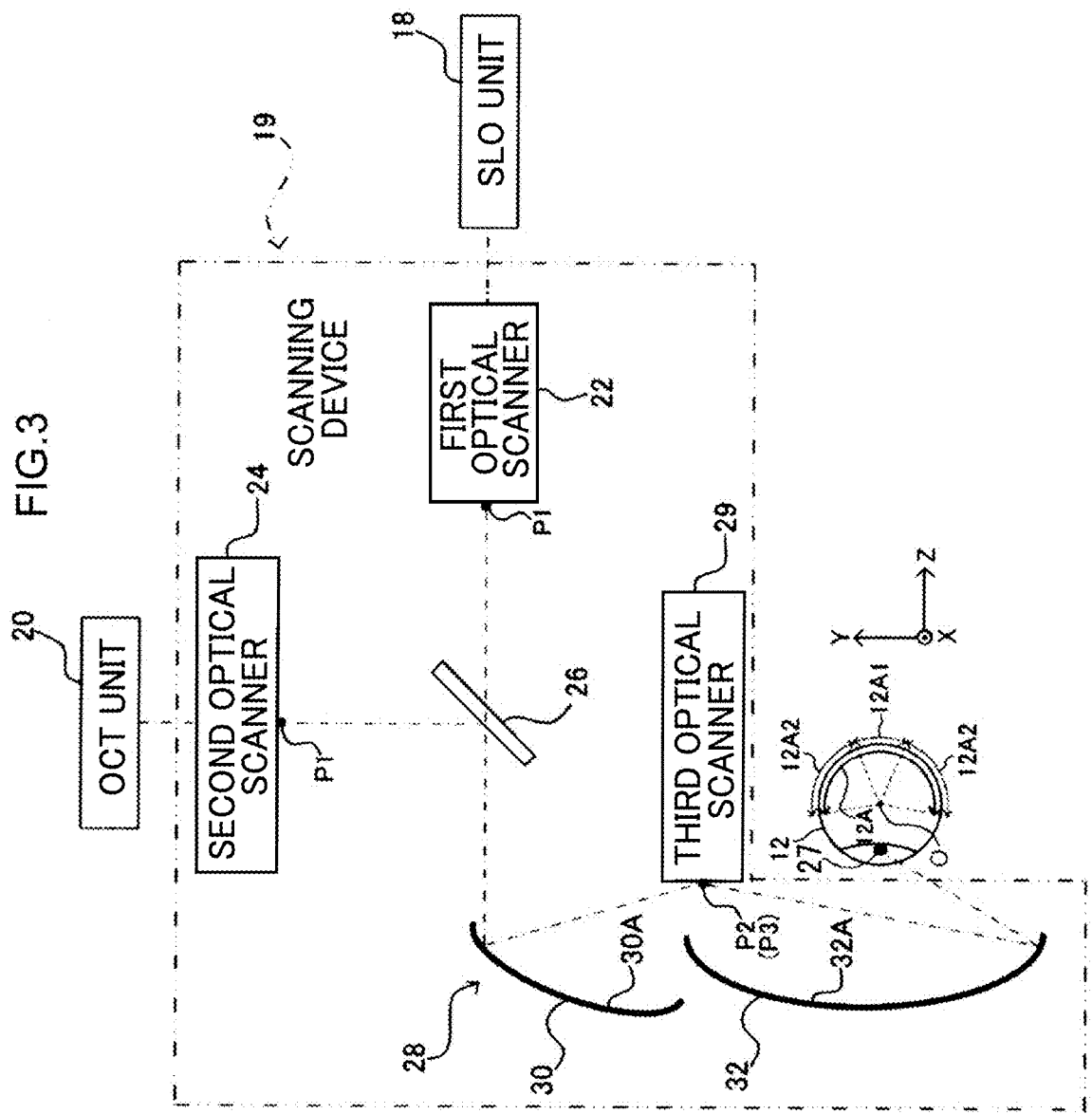
FIG. 3 is a diagram illustrating an example of a schematic configuration of a scanning device included in an ophthalmic imaging device.

Explanation follows regarding configuration of the scanning device 19 included in the ophthalmic imaging device 110, with reference to FIG. 3. As illustrated in FIG. 3, a common optical system 28 includes a slit mirror 30 and an elliptical mirror 32 as well as the third optical scanner 29. Note that the dichroic mirror 26, the slit mirror 30, and the elliptical mirror 32 are illustrated in an end-on side view. Note that the common optical system 28 may be configured by a set of plural lenses instead of by the slit mirror 30 and the elliptical mirror 32.

The slit mirror 30 includes an elliptical first reflecting face 30A. The first reflecting face 30A has first focal points P1 and a second focal point P2. The elliptical mirror 32 also includes an elliptical second reflecting face 32A. The second reflecting face 32A has a first focal point P3 and a second focal point P4.

The slit mirror 30, the elliptical mirror 32, and the third optical scanner 29 are disposed such that the first focal point P3 and the second focal point P2 are both located at a common position at the third optical scanner 29. The slit mirror 30, the elliptical mirror 32, and the third optical scanner 29 are also disposed such that the second focal point P4 is positioned at the center of the pupil of the subject eye 12. Moreover, the first optical scanner 22, the second optical scanner 24, and the slit mirror 30 are disposed such that the first focal points P1 are positioned at the first optical scanner 22 and the second optical scanner 24.

Namely, the first optical scanner 22, the second optical scanner 24, and the third optical scanner 29 are disposed at conjugate positions to the center of the pupil of the subject eye 12.

Note that the configurations disclosed in Japanese Patent Nos. 3490088 and 5330236 are the same as the basic configuration of the scanning device 19.

In the present exemplary embodiment, the scanning device illustrated in FIG. 3 has a field of view (FOV) angle of the fundus covering a greater angle than in technology hitherto, thereby enabling observation of a wider range of a fundus region than that achieved by technology hitherto. Explanation follows regarding the wider range of the fundus region, with a distinction being made between an external illumination angle of illumination light shone from the exterior by the ophthalmic imaging device 110 and an internal illumination angle serving as an angle illuminated within the subject eye by shining this illumination light.

The external illumination angle is an illumination angle of light from the ophthalmic imaging device 110 side, namely from the exterior of the subject eye 12. Namely, the external illumination angle is configured by the angle of light shone toward the fundus of the subject eye 12 heading toward a pupil center point 27 of the subject eye 12 (namely, a center point of the pupil as viewed face-on (see also FIG. 2)). The external illumination angle is equivalent to the angle of light reflected from the fundus so as to head from the pupil center point 27 and be emitted from the subject eye 12 toward the ophthalmic imaging device 110.

The internal illumination angle is an illumination angle of light effectively imaged when the scanning light is shone onto the fundus of the subject eye 12, with the eyeball center O of the subject eye 12 as a reference position. Although an external illumination angle A and an internal illumination angle B are in a correspondence relationship, since the following explanation relates to the ophthalmic imaging device, the external illumination angle is employed as an illumination angle corresponding to the field of view angle of the fundus.

The ophthalmic imaging device 110 performs image capture in the imageable region 12A (see also FIG. 2), this being a fundus region of the subject eye 12, using the external illumination angle. The imageable region 12A is, for example, the largest region capable of being scanned by the scanning light from the scanning device 19. One example of the imageable region 12A is the external illumination angle A, providing a field of view over a range of approximately 120°. In such cases, the internal illumination angle corresponds to an angle of approximately 160°.

For example, the imageable region 12A can be broadly split into a first imageable region 12A1 and a second imageable region 12A2. The first imageable region 12A1 is a range of a field of view in the vicinity of an axis of vision CL passing through the pupil center point 27 and the center O of the subject eye 12. The second imageable region 12A2 is a peripheral region to the first imageable region 12A1 and is a range in a peripheral field of view away from the axis of vision CL. An example of the external illumination angle corresponding to the first imageable region 12A1 is approximately 30° (corresponding to an internal illumination angle in the region of 45°), and an example of the external illumination angle corresponding to the second imageable region 12A2 is approximately 120° (corresponding to an internal illumination angle in the region of 160°).

A fundus image obtained by performing image capture of the imageable region 12A of the subject eye 12 with the ophthalmic imaging device 110 is a wider region than that of technology hitherto, and is thus referred to hereafter as an ultra-wide field (UWF) fundus image.

Figure 4:
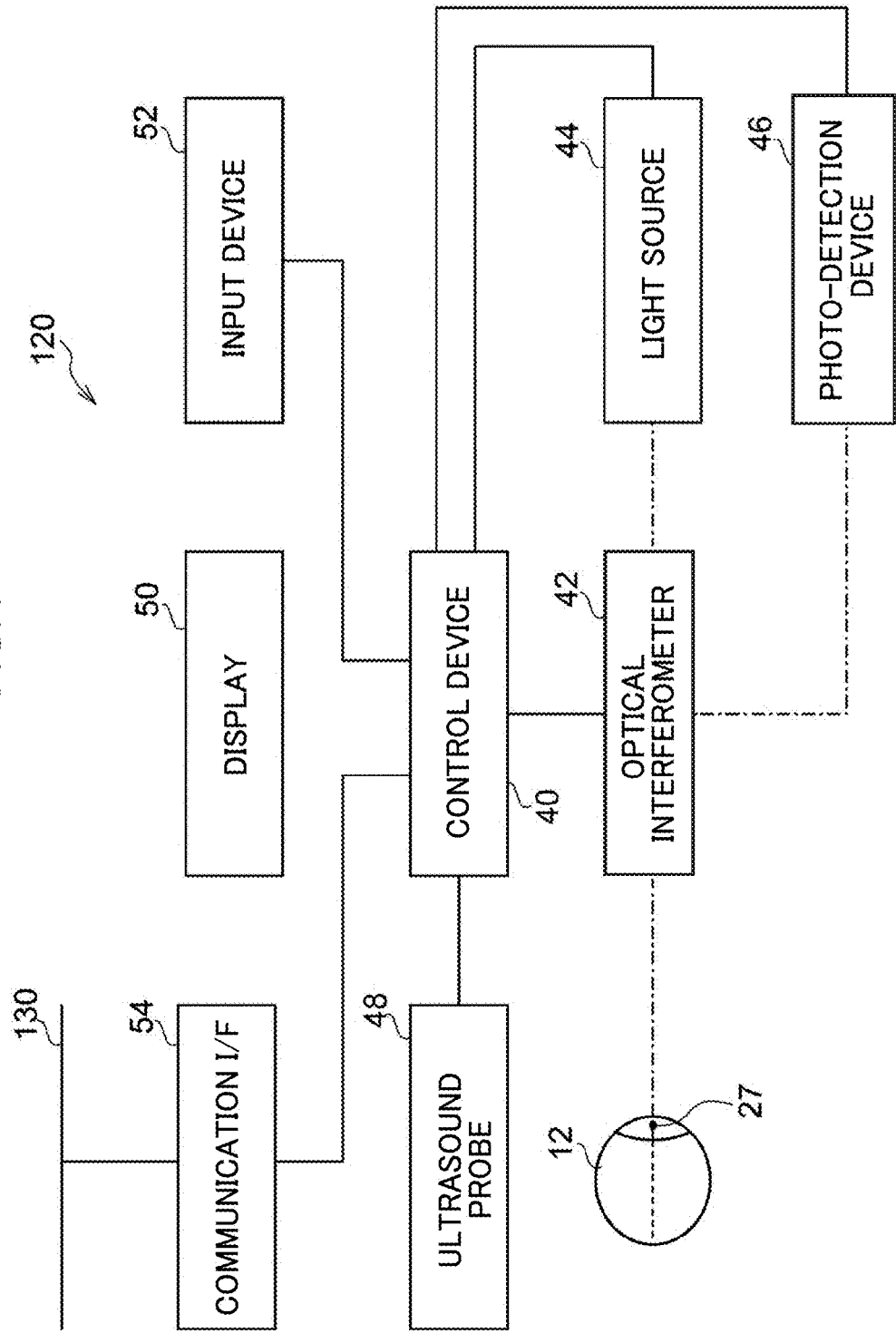
FIG. 4 is a diagram illustrating an example of an overall configuration of an eye axial length measurement device according to the first exemplary embodiment.

Explanation follows regarding an example of the eye axial length measurement device 120, with reference to FIG. 4.

As illustrated in FIG. 4, the eye axial length measurement device 120 includes an optical interferometer 42, a light source 44, a photo-detection device 46, an ultrasound probe 48, a display 50, an input device 52, a communication interface (I/F) 54, and a control device 40 controlling these respective devices (42 to 52). The control device 40 is configured by a computer including a non-illustrated CPU, ROM, RAM, secondary storage device, and the like. Although the example given here employs a single CPU, the technology disclosed herein is not limited thereto, and plural CPUs may be applied. The ultrasound probe 48 has a configuration capable of being held by the user, and is connected to the control device 40 through a non-illustrated cable.

The eye axial length measurement device 120 includes two modes for measuring the eye axial length, this being the axial direction length of the subject eye 12. A first mode is a mode in which the eye axial length is measured using the optical interferometer 42, the light source 44, and the photo-detection device 46. Specifically, for example, after light from the light source 44 has been guided into the subject eye 12, the optical interferometer 42 induces interference between light reflected from the fundus and light reflected from the cornea by adjusting the optical path length. The optical interferometer 42 then causes the light that has been introduced to interfere (interference light) to be photo-detected by the photo-detection device 46. The control device 40 measures the eye axial length based on an interference signal output from the photo-detection device 46. A second mode is a mode in which the eye axial length is measured using the ultrasound probe 48. Ultrasound waves from the ultrasound probe 48 are guided into the subject eye 12 in a state in which a tip of the ultrasound probe 48 is in contact with the subject eye 12, and the eye axial length is measured from the time between emitting and receiving the ultrasound waves. The first mode and the second mode can be set by input using the input device 52.

The eye axial length measurement device 120 transmits the eye axial length measured in the first mode or the second mode to the image management server 140 via the communication interface (I/F) 54 and the network 130. The eye axial length may be measured using both the first mode and the second mode, in which case the average of the eye axial length measured by the two modes is transmitted to the image management server 140 as the eye axial length.

The eye axial length measurement device 120 is widely known, for example as described in Japanese Patent No. 6094483 and in JP-A No. 2010-184048.

The eye axial length measurement device 120 further includes an inbuilt liquid crystal display (LCD) display, not illustrated in FIG. 4. The LCD displays a fixation target used to fix the gaze of the subject eye in a specific direction when measuring the eye axial length with the eye axial length measurement device 120. Light from the LCD passes through an optical system 58 including a lens and a mirror and is incident to the subject eye 12 such that the fixation target is projected onto the fundus of the subject eye 12.

Directions relative to the subject eye 12 are defined in the same way as those of the ophthalmic imaging device 110, and so explanation thereof is omitted.

In the present disclosure, the eye axial length refers to the distance from the front surface of the cornea to the surface of the retina of the subject eye 12 on a straight line passing through the pupil center point 27. When optical eye axial length measurement is performed in the above-described first mode by the eye axial length measurement device 120, when measurement light from the light source 44 is incident to the subject eye 12, the eye axial length is measured based on different measurement positions on the fundus, these being dependent on the position where the measurement light is incident on the front surface of the cornea and the angle of incidence (see FIG. 7).

Figure 5A:
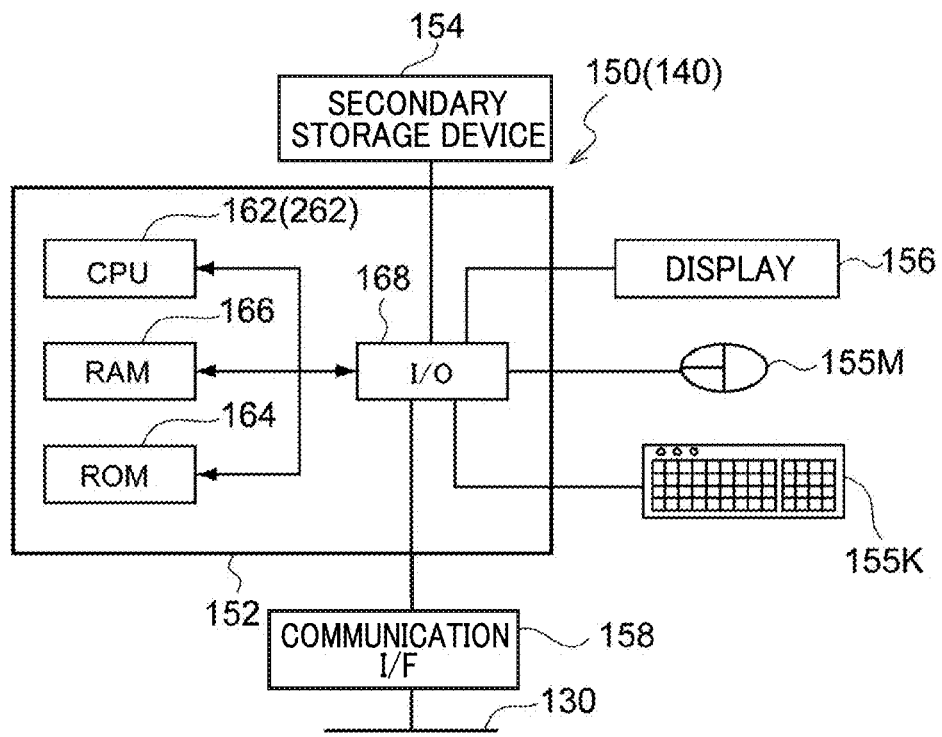
FIG. 5A is a block diagram illustrating relevant configuration of an electrical system of an image viewer according to the first exemplary embodiment.

Explanation follows regarding configuration of an electrical system of the image viewer 150, with reference to FIG. 5A. As illustrated in FIG. 5A, the image viewer 150 includes a computer body 152 configured including a CPU 162, RAM 166, ROM 164, and an input/output (I/O) port 168. Although the example given here employs a single CPU, the technology disclosed herein is not limited thereto, and plural CPUs may be applied. A secondary storage device 154, a display 156, a mouse 155M, a keyboard 155K, and a communication interface (I/F) 158 are connected to the input/output (I/O) port 168 of the computer body 152. The input/output (I/O) port 168 of the computer body 152 is connected to the network 130 through the communication interface (I/F) 158, enabling communication with the ophthalmic imaging device 110 and the image management server 140. The ROM 164 or the secondary storage device 154 is stored with a three-dimensional fundus image generation program, described below. Note that the three-dimensional fundus image generation program is an example of a program of the technology disclosed herein.

Figure 5B:
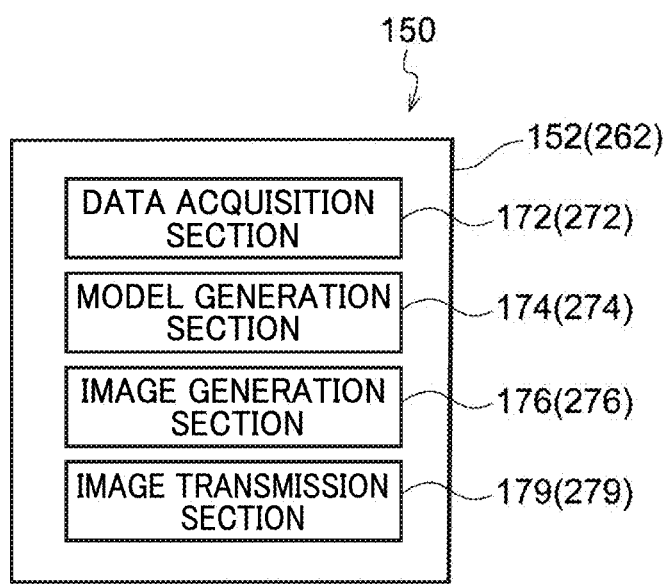
FIG. 5B is a block diagram illustrating functionality of an image viewer according to the first exemplary embodiment.

Explanation follows regarding functional configuration of the three-dimensional fundus image generation program executed by the CPU 162 of the image viewer 150, with reference to FIG. 5B. As illustrated in FIG. 5B, the three-dimensional fundus image generation program includes a data acquisition function, a model generation function, an image generation function, and an image transmission function. The CPU 162 of the image viewer 150 executes the three-dimensional fundus image generation program with this functionality, such that the CPU 162 of the image viewer 150 functions as a data acquisition section 172, a model generation section 174, an image generation section 176, and an image transmission section 179. Note that the model generation section 174 is an example of a first output section or a first image generation section of the present disclosure. The image generation section 176 is an example of a generation section, a second output section, or a second image generation section of the present disclosure. The image transmission section 179 is an example of an image signal output section of the present disclosure.

Configuration of an electrical system of the image management server 140 is similar to the configuration of the electrical system of the image viewer 150, and so explanation thereof is omitted.

Modified Example of System Configuration

In the foregoing explanation, the system configuration of the first exemplary embodiment is made up of four independent pieces of hardware. However, the system configuration is not limited thereto. For example, the ophthalmic imaging device 110 and the eye axial length measurement device 120 may be integrated together. In such cases, the eye axial length of the subject eye 12 is measured using a tomographic image of the cornea and a tomographic image of the retina obtained by OCT imaging by the ophthalmic imaging device 110. Alternatively, the ophthalmic imaging device 110, the eye axial length measurement device 120, and the image management server 140 may all be integrated together.

Three-Dimensional Fundus Image Generation and Recording Process

Detailed explanation follows regarding generation and recording of a three-dimensional fundus image of the first exemplary embodiment.

In the fundus image display system 100 according to the first exemplary embodiment, the ophthalmic imaging device 110 images a two-dimensional fundus image of the subject eye 12 to create fundus image data and then transmits the fundus image data to the image management server 140 via the network 130. Next, the eye axial length measurement device 120 measures plural eye axial lengths of the subject eye 12 to create eye axial length data, and then transmits the eye axial length data to the image management server 140 via the network 130. The image viewer 150 receives the fundus image data and the eye axial length data for the subject eye 12 from the image management server 140 and generates a three-dimensional fundus image of the subject eye 12.

In the interest of convenience, the following explanation splits the three-dimensional fundus image generation and recording processing into three parts, namely: (1) imaging of a two-dimensional fundus image; (2) measurement of eye axial length; and (3) processing executed by the image viewer 150.

Imaging of Fundus Image

Explanation follows regarding an example in which the two-dimensional fundus image of the first exemplary embodiment is a two-dimensional image of a fixed region within the imageable region 12A of the subject eye 12, imaged using the SLO imaging system function of the ophthalmic imaging device 110.

Figure 6:
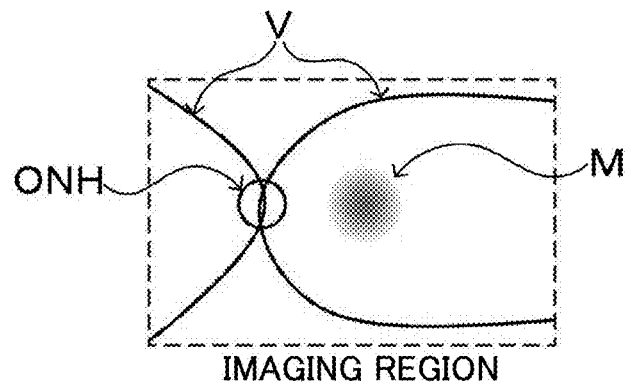
FIG. 6 is a diagram illustrating an example of a two-dimensional fundus image imaged by an ophthalmic imaging device.

FIG. 6 schematically illustrates an example of a two-dimensional image of the fundus of the subject eye 12. The image in FIG. 6 is a fixed region within the imageable region 12A of the subject eye 12 imaged by the SLO imaging system function of the ophthalmic imaging device 110. As described above, the ophthalmic imaging device 110 is capable of imaging a UWF fundus image. Employing a UWF fundus image enables discrimination of blood vessels V of the retina, an optic nerve head ONH, and the macula M, these being examples of biological feature points in the subject eye 12, as well as discrimination of the fovea centralis at the center of the macula M and the like.

Note that when the ophthalmic imaging device 110 executes the SLO imaging system function to acquire a two-dimensional image of the fixed region within the imageable region 12A of the subject eye 12 the imageable region 12A is scanned with SLO light in the X direction (horizontal direction) by the first optical scanner 22 and in the Y direction (vertical direction) by the third optical scanner 29, as previously described. When scanning in these two directions, a point within the imageable region 12A corresponds to a pair of angles $(\varphi_X, \varphi_Y)$. For example, when taking a straight line connecting the pupil center point 27 and the eyeball center O as a reference axis, $\varphi_X$ is an angle in the horizontal direction between the SLO light incident to the subject eye 12 and heading toward the pupil center point 27 and the reference axis, and $\varphi_Y$ is the angle in the vertical direction between the incident SLO light and the reference axis.

When values of a pair of angles $(\varphi_X, \varphi_Y)$ have been specified, a point in the imageable region 12A corresponding to these values is then imaged. The ophthalmic imaging device 110 according to the first exemplary embodiment stores the values $(\varphi_X, \varphi_Y)$ when scanning with the SLO light in the horizontal direction and the vertical direction. The values $(\varphi_X, \varphi_Y)$ are, for example, stored in the RAM of the control device 16. The stored values $(\varphi_X, \varphi_Y)$ are employed in a position determination process, described later.

The control device 16 of the ophthalmic imaging device 110 transmits imaged SLO fundus image data to the image management server 140 via the network 130. A non-illustrated control device of the image management server 140 associates the received SLO fundus image data with the ID of the subject corresponding to the subject eye 12, and records this in a non-illustrated secondary storage device.

Note that the values $(\varphi_X, \varphi_Y)$ corresponding to the respective pixels in the SLO fundus image are associated with the fundus image data, and are transmitted from the ophthalmic imaging device 110 to the image management server 140 where they are recorded therein. Although not described each time in the interest of avoiding repetition, hereafter the fundus image data is assumed to be fundus image data associated with the values ($\varphi_X$, $\varphi_Y$) corresponding to the respective pixels in the fundus image.

The two-dimensional fundus image in the foregoing explanation is configured by an SLO image. However, the two-dimensional fundus image is not limited to an SLO image, and may be a two-dimensional planar image (for example a tomographic image of the retina and/or an en-face image) created using OCT volume data imaged using the OCT imaging system function of the ophthalmic imaging device 110.

Eye Axial Length Measurement

As described above, in the present disclosure, the eye axial length is the distance from the front surface of the cornea to the surface of the retina of the subject eye 12 when passing through the pupil center point 27. As an example, in the following explanation the eye axial length measurement device 120 operates in the first mode to perform optical eye axial length measurement.

Figure 7:
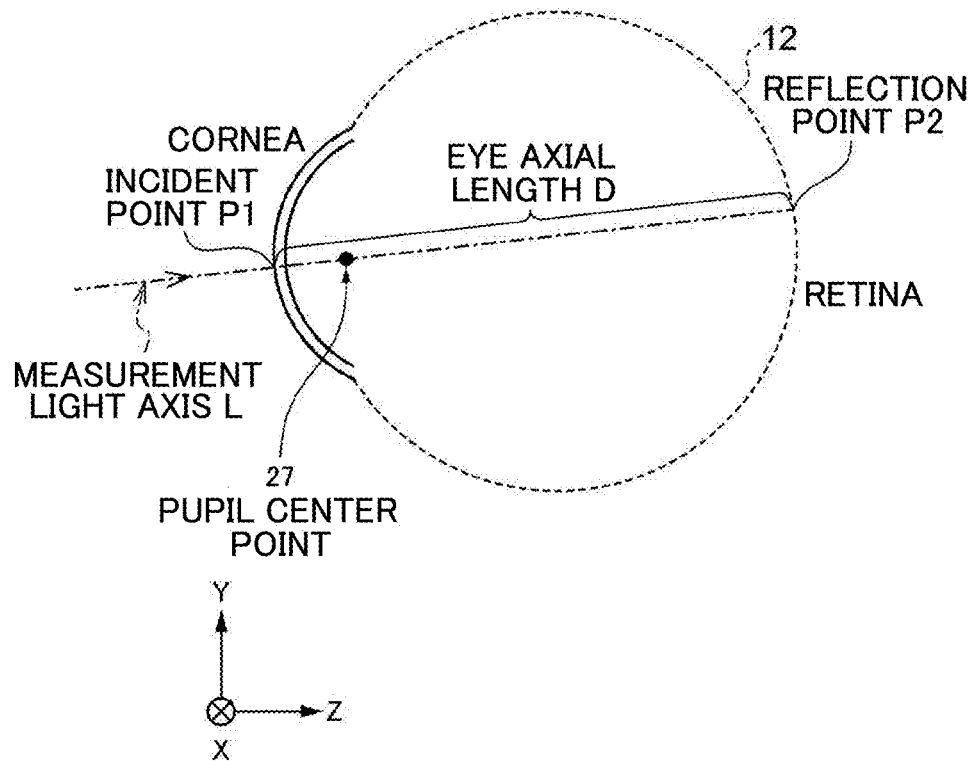
FIG. 7 is a diagram illustrating a definition of eyeball length in the present disclosure.

FIG. 7 illustrates an example of eye axial length in the first exemplary embodiment. FIG. 7 illustrates an axis of measurement light from the eye axial length measurement device 120 with respect to the subject eye 12, an incident point P1 at the intersection between the measurement light and the front surface of the cornea, and a reflection point P2 at the intersection between the measurement light and the retinal surface. An eye axial length D is defined as the distance between the incident point P1 and the reflection point P2.

The eye axial length in the first exemplary embodiment is an amount determined by the position of the incident point P1 and the angle of incidence of the measurement light to the retinal surface at the incident point P1. The eye axial length is one type of shape information expressing the shape of the subject eye 12 in the present disclosure. The shape of the subject eye 12 can be estimated by changing the position of the incident point P1 and the angle of incidence of the measurement light to the incident point P1 and measuring plural eye axial lengths.

In particular, in the first exemplary embodiment it is assumed based on medical knowledge that the shape of the subject eye 12 can be approximated by any one out of five predetermined eyeball models (see FIG. 12), as will be described later. Accordingly, it is thought that eye axial length measurements taken for at least three suitably set incident point P1 and incident angle combinations should be sufficient.

Figure 8A:
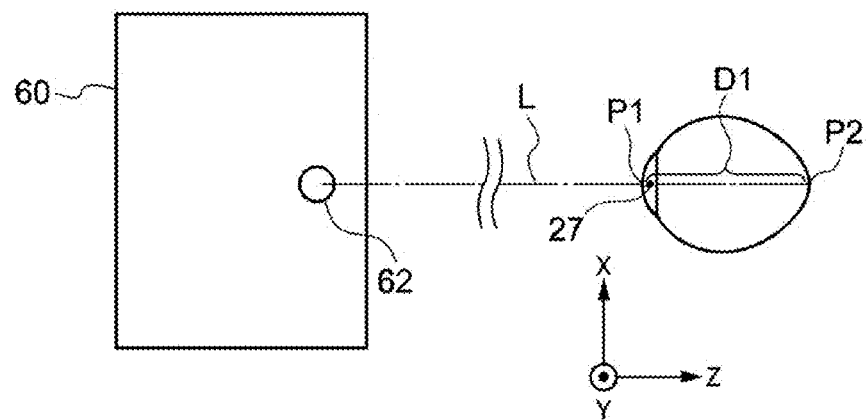
FIG. 8A to FIG. 8C are diagrams illustrating examples of measurement of eyeball length in the present disclosure.
Figure 8B:
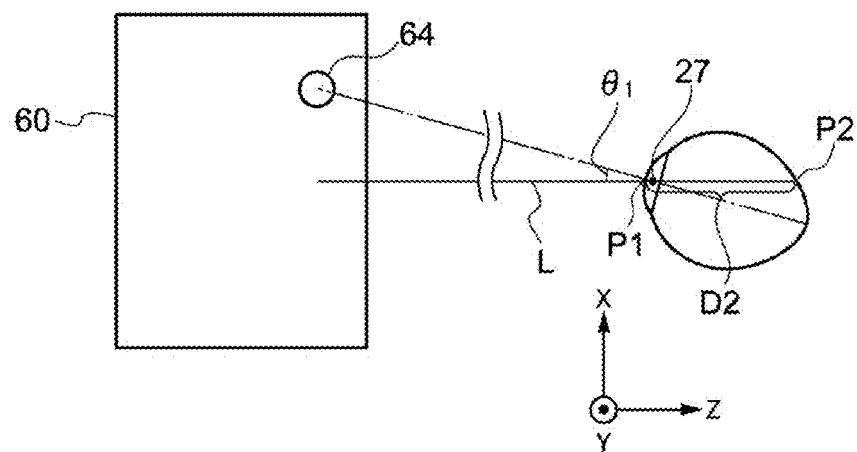
Figure 8C:
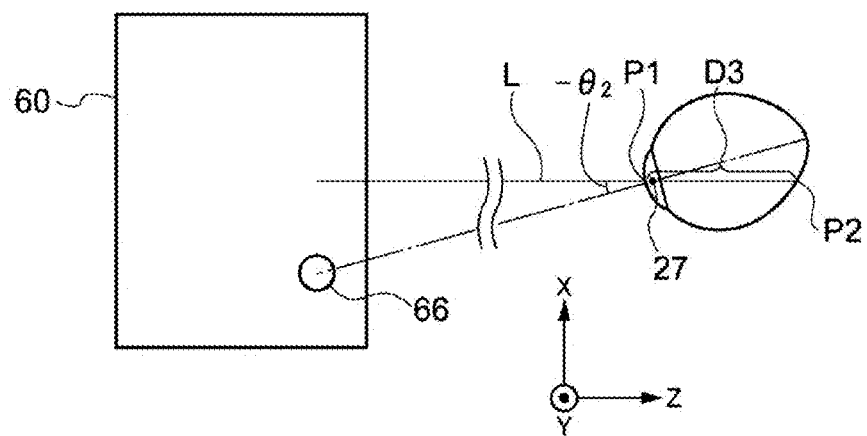

FIG. 8A to FIG. 8C illustrate an example of three eye axial length measurements of the subject eye 12 using three incident point P and incident angle combinations. FIG. 8A to FIG. 8C are cross-sections illustrating the subject eye 12 as sectioned along the X-Z plane. Although the origin of the coordinate axes in the above-described coordinate system are not specified, in FIG. 8A to FIG. 8C and the following explanation, the eyeball center O of the subject eye 12 is assumed to be in a horizontal plane where Y=0 as an example. However, the position of the origin (namely the horizontal plane in which the eye axial length is measured) is not limited thereto, and any cross-section where suitable eye axial length measurements can be assumed to estimate the shape of the subject eye 12 may be employed.

FIG. 8A to FIG. 8C illustrate an LCD 60 used to project the fixation target onto the fundus of the subject eye 12. Light from the LCD 60 is incident to the subject eye 12, and thus projects the fixation target onto the fundus of the subject eye 12. Note that as previously mentioned, the LCD 60 is not illustrated in FIG. 4.

The LCD 60 is configured to be capable of illuminating plural fixation positions in the X direction in the horizontal plane (X-Z plane) illustrated in FIG. 8A to FIG. 8C. In FIG. 8A, the LCD 60 illuminates a fixation position 62, this being a fixation position where the visual axis of the subject eye 12 corresponds to an axis L of the measurement light from the eye axial length measurement device 120. Under the settings illustrated in FIG. 8A, the eye axial length measured by the eye axial length measurement device 120 is an eye axial length D1.

In FIG. 8B, the LCD 60 illuminates a fixation position 64 positioned in a positive X direction with respect to the fixation position 62 such that the visual axis of the subject eye 12 forms an angle $\theta_1$ with respect to the axis L of the measurement light. In FIG. 8C, the LCD 60 illuminates a fixation position 66 positioned in a negative X direction with respect to the fixation position 62 such that the visual axis of the subject eye 12 forms an angle $-\theta_2$ with respect to the axis L of the measurement light. Under the settings illustrated in FIG. 8B and FIG. 8C, the eye axial lengths measured by the eye axial length measurement device 120 are eye axial lengths D2, D3.

Note that in the interests of simplicity, a direction toward the positive direction of the X axis forms an angle $\theta$ in a positive direction.

The fixation position illuminated by the LCD 60 is changed as described above to obtain the three eye axial lengths D1, D2, D3 based on the positions of the incident points P1 and the three measurement positions with changed incident angles $\theta$ in the X-Z plane of the measurement light with respect to the retinal surface at the corresponding incident point P1. Note that the eye axial lengths D1, D2, D3 are an example of eyeball shape information of the present disclosure.

Figure 9:
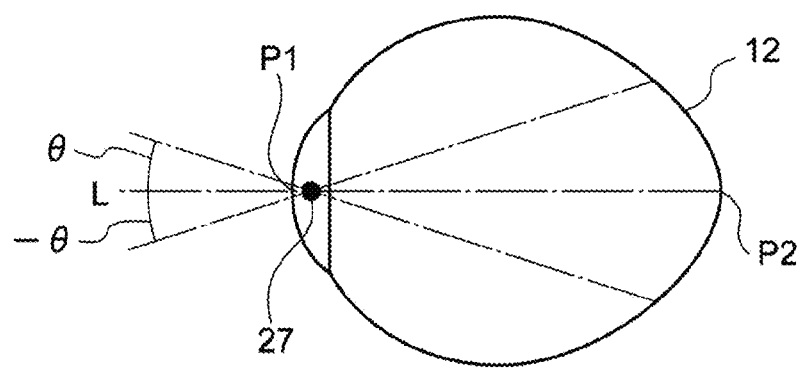
FIG. 9 is a diagram illustrating another example of measurement of eyeball length in the present disclosure.

As illustrated in FIG. 9, as an example the fixation positions 64 and 66 may be set such that $\theta_1=\theta_2=\theta$. This facilitates understanding of symmetry in the shape of the subject eye 12 about the horizontal plane. Information relating to symmetry about the horizontal plane in the subject eye is thought to be useful when discriminating between the five eyeball models (see FIG. 12) described later. In the following explanation, $\theta_1=\theta_2=\theta$.

Although the three eye axial lengths are measured in the same horizontal plane by changing the fixation position illuminated by the LCD in the X-Z plane (horizontal plane) in the foregoing explanation, the measurement method of the plural eye axial lengths in the first exemplary embodiment is not limited thereto. For example, the fixation position illuminated by the LCD 60 may be changed in the Y direction (namely, the vertical direction) to measure the plural eye axial lengths. It is sufficient that the eye axial length measurement be capable of assisting deduction as to which of the five eyeball models described later the subject eye 12 corresponds to.

The control device 40 of the eye axial length measurement device 120 transmits eye axial length data relating to the three measured eye axial lengths to the image management server 140 via the network 130. The eye axial length data includes the value of the angle $\theta$ and the subject ID in addition to the values of the three eye axial lengths D1, D2, D3. The non-illustrated control device of the image management server 140 associates the received eye axial length data with the subject ID corresponding to the subject eye 12, and records this in the non-illustrated secondary storage device.

The eye axial length measurement method employed is not limited to employing OCT. In cases in which the eye axial length measurement device 120 operates in the second mode employing an ultrasound signal, the eye axial length of the subject eye 12 may be measured using the ultrasound signal.

In cases in which the eye axial length measurement device 120 operates in both the first mode and the second mode, OCT and an ultrasound signal may be employed in conjunction to measure the eye axial length of the subject eye 12.

Processing Executed by Image Viewer 150

In the first exemplary embodiment, a three-dimensional eyeball model is generated as a result of a user decision assisted by the fundus image display system 100. Specifically, the image viewer 150 displays an eye axial length measurement result of the eye axial length measurement device 120 received from the image management server 140 and plural eyeball model candidates on the display 156 at the same time, and prompts the user to select the one eyeball model candidate most appropriate to the subject eye 12 currently being observed. The user considers the content displayed on the display 156 and selects the eyeball model candidate they consider most suitable, thereby deciding on the three-dimensional eyeball model. The CPU 162 of the image viewer 150 then performs image processing to wrap the two-dimensional fundus image imaged by the ophthalmic imaging device 110 onto the three-dimensional eyeball model so as to generate a three-dimensional fundus image.

Note that as an example, the three-dimensional fundus image refers to an image that appears to be three-dimensional, due to being generated by image processing to wrap the two-dimensional fundus image imaged by the SLO unit of the ophthalmic imaging device 110 onto the surface of the three-dimensional eyeball model. However, the three-dimensional fundus image is not limited thereto. For example, an image may be employed expressing the three-dimensional structure of the retina by employing OCT volume data obtained for a fixed region of the fundus of the subject eye 12 from the OCT imaging system function of the ophthalmic imaging device 110. Alternatively, a three-dimensional structure of the retina obtained using OCT volume data may be set as an eyeball model.

Figure 10:
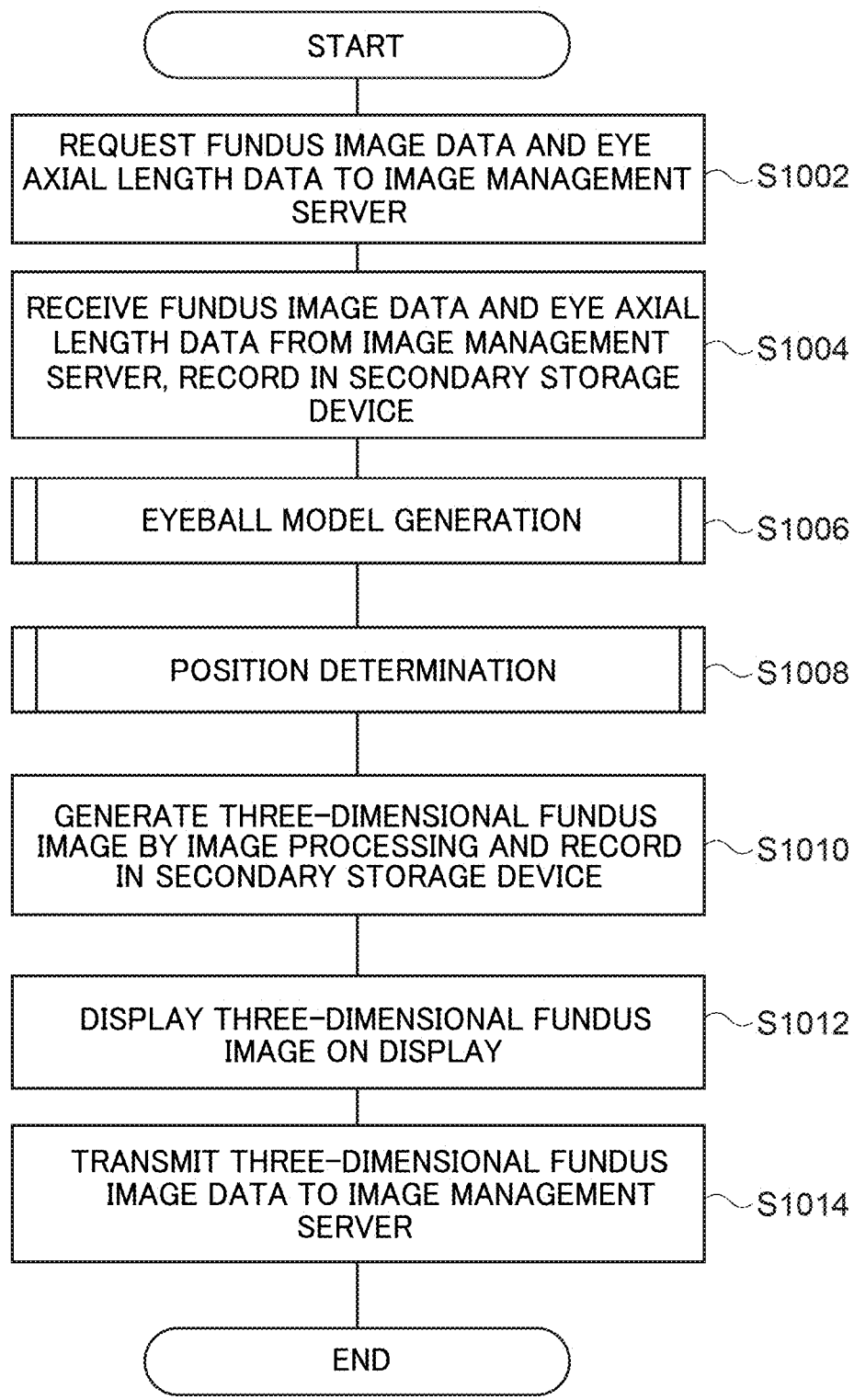
FIG. 10 is a flowchart illustrating an example of a program executed by a CPU of an image viewer according to the first exemplary embodiment.
Figure 12A:
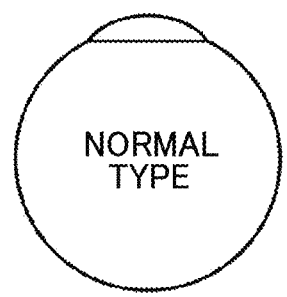
FIG. 12A to FIG 12E are diagrams illustrating five types of eyeball model.
Figure 12B:
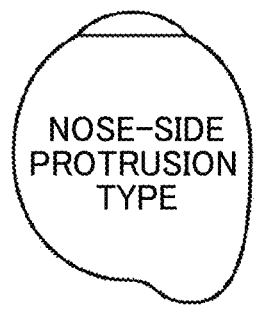
Figure 12C:
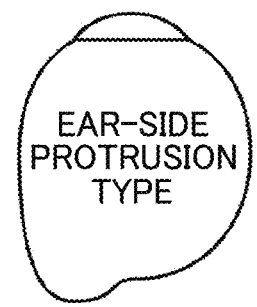
Figure 12D:
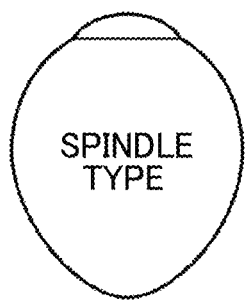
Figure 12E:
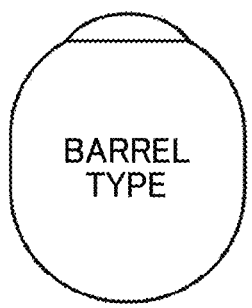
Figure 15:
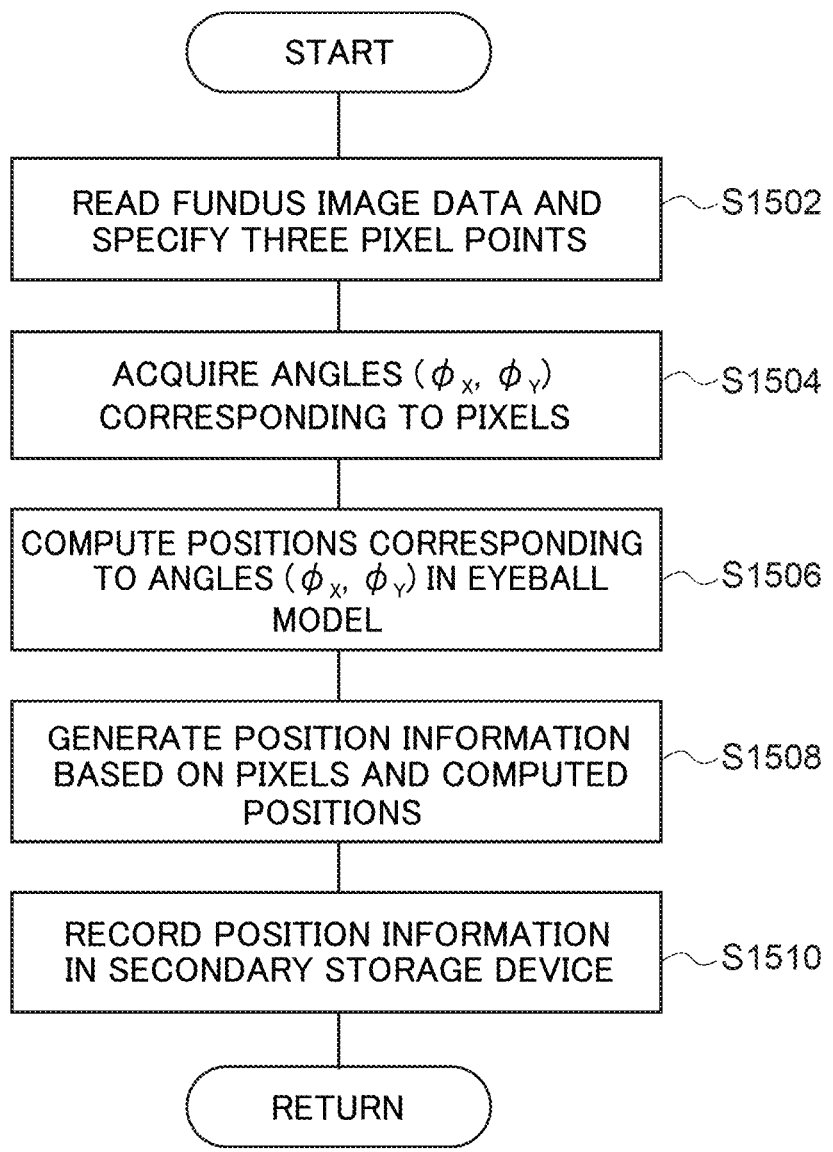
FIG. 15 is a flowchart illustrating contents of a position determination sub-routine according to the first exemplary embodiment.

FIG. 10, FIG. 11, and FIG. 15 are flowcharts each illustrating an example of a processing program to perform three-dimensional fundus image display in the first exemplary embodiment. FIG. 10, FIG. 11, and FIG. 15 each illustrate an example of a processing program executed by the image viewer 150.

Specifically, the processing program executed by the image viewer 150 is executed by the CPU 162 of the image viewer 150 functioning as the data acquisition section 172, the model generation section 174, the image generation section 176, and the image transmission section 179. Communication between the image viewer 150 and the image management server 140 is performed via the network 130.

Here, it is assumed that imaging of the two-dimensional fundus image by the ophthalmic imaging device 110 and measurement of the three eye axial lengths by the eye axial length measurement device 120 have already been completed for the subject eye 12 of the subject, and that two-dimensional fundus image data and eye axial length data have been recorded in the non-illustrated secondary storage device of the image management server 140. A user wishing to generate and display a three-dimensional fundus image inputs this intention to the image viewer 150 by operating the mouse 155M or the keyboard 155K. This starts execution of the processing program illustrated in FIG. 10, FIG. 11, and FIG. 15 by the image viewer 150, and starts a processing process to perform three-dimensional fundus image display according to the first exemplary embodiment. FIG. 10 is a flowchart illustrating the overall processing process.

In the interests of simplicity, in the following explanation the overall three-dimensional fundus image display processing is split into three: (A) deciding on the eyeball model; (B) position determination; and (C) three-dimensional fundus image creation and display.

A: Eyeball Model Generation

The data acquisition section 172 executes the processing at steps S1002, S1004 in FIG. 10. The model generation section 174 executes the processing at step S1006 in FIG. 10.

At step S1002, the data acquisition section 172 employs the subject ID and so on input to the image viewer 150 to transmit a request to the image management server 140 in order to acquire the two-dimensional fundus image data and the eye axial length data corresponding to the subject eye 12 to be diagnosed by an ophthalmologist. This request includes the subject ID corresponding to the subject eye 12.

When the image management server 140 receives this request from the image viewer 150, the control section of the image management server 140 identifies data corresponding to the subject eye 12 of the subject based on the ID. The control section of the image management server 140 then reads the two-dimensional fundus image data and the eye axial length data corresponding to the ID recorded in the secondary storage device, and transmits these to the image viewer 150.

When the image viewer 150 receives the two-dimensional fundus image data and the eye axial length data corresponding to the subject eye 12 from the image management server 140, at step S1004, the data acquisition section 172 records the received two-dimensional fundus image data and eye axial length data in the secondary storage device 154.

Note that as previously described, the values $(\varphi_X, \varphi_Y)$ corresponding to the respective pixels in the two-dimensional fundus image are associated with the two-dimensional fundus image data.

Next, processing transitions to step S1006. The processing described hereafter is executed by the model generation section 174.

The eyeball model generation process of the first exemplary embodiment is illustrated as a sub-routine in FIG. 11. FIG. 11 illustrates a sub-routine as an example of the processing program executed by the CPU 162 of the image viewer 150 serving as the model generation section 174.

At step S1102, the model generation section 174 reads the eye axial length data from the secondary storage device 154 and displays the three eye axial lengths D1, D2, D3 corresponding to the subject eye 12 of the subject on a display screen of the display 156.

When this is performed, the model generation section 174 displays the three eye axial lengths D1, D2, D3 (see FIG. 13 and FIG. 14) together with the five eyeball model candidates on the display screen of the display 156.

It is known from medical knowledge that at least in the case of eyeballs of Japanese people, deformation of the eyeball due to pathological myopia can be classified into the following four types. Explanation follows regarding this point.

A first type is a nose-side protrusion type, in which left-right asymmetry is present about a central axis running parallel to the Z axis and the retina protrudes in a direction toward the nose as observed in cross-section sectioned along the X-Z plane (this is also referred to as a nose-side deviation type). A second type is an ear-side protrusion type in which left-right asymmetry is present about a central axis running parallel to the Z axis and the retina protrudes in a direction toward the ear as observed in cross-section sectioned along the X-Z plane (this is also referred to as an ear-side deviation type). A third type is a spindle type in which there is left-right symmetry about a central axis running parallel to the Z axis and the vicinity of the fovea centralis of the retina is pointed as observed in cross-section sectioned along the X-Z plane (this is also referred to as a strawberry type). A fourth type is a barrel type in which there is left-right symmetry about a central axis running parallel to the Z axis and the vicinity of the fovea centralis of the retina protrudes in a rounded manner as observed in cross-section sectioned along the X-Z plane.

When a normal eyeball that is not deformed by disease or the like is added to the four shapes described above, eyeballs can be classified into five types. FIG. 12 illustrates these five types. FIG. 12 illustrates diagrams of the left eyeballs of subjects observed along a positive direction of the Y axis (namely, observed from vertically above), A being a normal type, B being a nose-side protrusion type, C being an ear-side protrusion type, D being a spindle type, and E being a barrel type. In the following explanation, the subject eye 12 is assumed to be the left eyeball of the subject.

Figure 13:
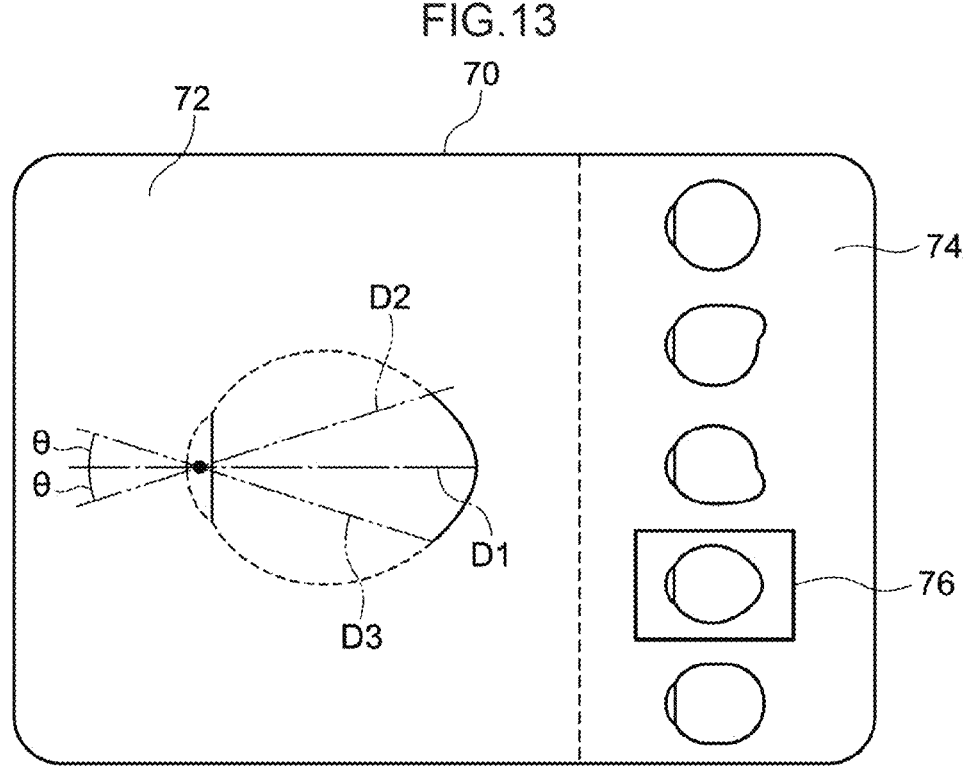
FIG. 13 is a diagram illustrating an example of an eyeball model selection screen according to the first exemplary embodiment.

Explanation now returns to the sub-routine illustrated in FIG. 11. FIG. 13 illustrates an example of a selection image 70 that the model generation section 174 displays on the display screen of the display 156 at step S1102. The selection image 70 in FIG. 13 includes an eye axial length display region 72 and an eyeball model candidate display region 74. Note that the selection image 70 is an example of an eyeball model selection screen of the present disclosure. A signal output by the model generation section 174 in order to display the selection image 70 on the display screen of the display 156 is an example of a first image signal of the present disclosure.

The five eyeball types illustrated in FIG. 12 are displayed in the eyeball model candidate display region 74 in FIG. 13. The eyeball model candidate display region 74 also displays a selection frame 76. The selection frame 76 is employed in selection and emphatic display of one eyeball type in the eyeball model candidate display region 74. A user operates the mouse 155M or the keyboard 155K of the image viewer 150 to move the selection frame 76 up and down on the display screen of the display 156, and is thereby able to select one eyeball model candidate from out of the five eyeball model candidates displayed in the eyeball model candidate display region 74.

Five graphics representing the five types of eyeball model may be displayed in the eyeball model candidate display region 74. Alternatively, text representing the names of the five types of eyeball model (eyeball model names: normal type, nose-side protrusion type, ear-side protrusion type, spindle type, and barrel type), or a combination of graphics and text may be displayed in the eyeball model candidate display region 74.

In the eye axial length display region 72 in FIG. 13, an eyeball image annotated with the three eye axial lengths D1, D2, D3 of the subject eye 12 measured by the eye axial length measurement device 120 is displayed within an outline corresponding to the outline of the eyeball model candidate emphatically displayed by the selection frame 76 in the eyeball model candidate display region 74. The outline displayed in the eye axial length display region 72 corresponds to an outline of the eyeball of the subject eye 12 in cross-section sectioned along an X-Z plane corresponding to a flat plane with the eyeball center O at Y=0.

Specifically, the model generation section 174 decides on the size of the outline of the eyeball image displayed in the eye axial length display region 72 based on the size of the eye axial length D1. As an example, the outline of the eyeball image is decided such that the eye axial length D1 passes through the eyeball center O, and end points of the eye axial length D1 are disposed at a portion corresponding to the cornea and a location corresponding to the retina (namely, such that the eye axial length D1 fits exactly inside the outline). The model generation section 174 then employs the angle θ included in the eye axial length data stored in the secondary storage device 154 to dispose the eye axial lengths D2 and D3 within the outline of the eyeball image so as to form the respective angles θ and −θ with respect to D1. As an example, the eye axial lengths D2 and D3 are disposed such that the start points of the eye axial lengths D2 and D3 are set at locations of the outline corresponding to the cornea.

In the example illustrated in FIG. 13, the spindle type model D is emphatically displayed by the selection frame 76 in the eyeball model candidate display region 74. The outline of the spindle type model D with a size decided based on the size of the eye axial length D1, and the three eye axial lengths D1, D2, D3 within the outline, are displayed in the eye axial length display region 72.

Figure 14:
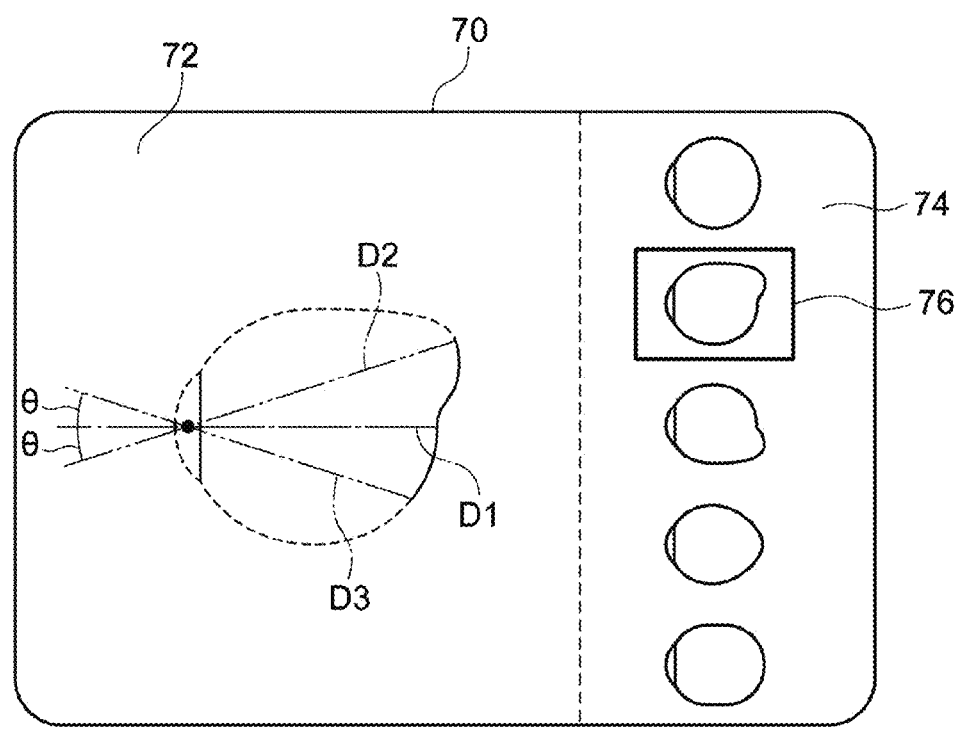
FIG. 14 is a diagram illustrating another example of an eyeball model selection screen according to the first exemplary embodiment.

It should be noted that in the eye axial length display region 72 in FIG. 14, a retina-side end point of the eye axial length D2 protrudes from a location of the outline corresponding to the retina in the eyeball image. This enables a user observing the eye axial length display region 72 illustrated in FIG. 14 to deduce that that the spindle type model D is unsuitable since the retina of the subject eye 12 protrudes in the direction of the nose.

Hereupon the user may conceivably operate the mouse 155M or the keyboard 155K of the image viewer 150 to move the selection frame 76 up or down in the eyeball model candidate display region 74 so as to emphatically display another eyeball model candidate. In the example illustrated in FIG. 14, the nose-side protrusion type model B is emphatically displayed by the selection frame 76 in the eyeball model candidate display region 74.

The outline of the nose-side protrusion type model B with a size decided based on the size of the eye axial length D1, and the three eye axial lengths D1, D2, D3 within the outline, are displayed in the eye axial length display region 72 in FIG. 14. Note that unlike in the example illustrated in FIG. 14, the eye axial length D2 does not protrude from the outline of the eyeball image in the eye axial length display region 72 in FIG. 13, and fits suitably within the outline. This enables the user observing the eye axial length display region 72 illustrated in FIG. 14 to deduce that the nose-side protrusion type model B is appropriate as an eyeball model for the subject eye 12, since the eye axial lengths D2 and D3 fit suitably within the outline.

The above-described method enables a user viewing the display screen of the display 156 of the image viewer 150 to observe a positional relationship between the outline and the eye axial lengths D2 and D3 in the eye axial length display region 72 while operating the mouse 155M or the keyboard 155K to move the selection frame 76 up and down in the eyeball model candidate display region 74, and to thereby decide which eyeball model candidate out of the five eyeball model candidates is most appropriate as an eyeball model for the subject eye 12.

Renewed explanation follows regarding the sub-routine serving as an example of the processing program executed by the model generation section 174, with reference to FIG. 11.

At step S1102, the model generation section 174 reads the eye axial length data from the secondary storage device 154, and displays the eye axial length display region 72 and the eyeball model candidate display region 74 on the display screen of the display 156 of the image viewer 150 as illustrated in FIG. 13 and FIG. 14. As an example, the normal type model A is selected at a start timing of the sub-routine. Namely, at step S1102 at the start timing of the sub-routine, the normal type model A is emphatically displayed in the eyeball model candidate display region 74 by the selection frame 76, and the outline of the normal type model A with a size decided based on the size of the eye axial length D1, and the three eye axial lengths D1, D2, D3 within the outline, are displayed in the eye axial length display region 72.

The user observing the eye axial length display region 72 operates the mouse 155M or the keyboard 155K to input a selection instruction or a decision instruction. The selection instruction is an instruction to select another eyeball model candidate instead of the eyeball model candidate currently selected (namely, currently emphatically displayed by the selection frame 76 in the eyeball model candidate display region 74). An example thereof would be an instruction to select the ear-side protrusion type model C instead of the normal type model A. The decision instruction is an instruction to decide that the eyeball model candidate currently selected is an appropriate eyeball model for the subject eye 12.

For example, the user is able to input a selection instruction by operating the mouse 155M to move a cursor displayed on the display screen of the display 156 to the position of an eyeball model candidate for selection, and left-clicking the mouse 155M. For example, the user is able to input a decision instruction by pressing the Return key on the keyboard 155K.

When any instruction is input by the user, processing transitions to step S1104. At step S1104, the model generation section 174 acquires the instruction input by the user.

At step S1106, the model generation section 174 determines whether or not the acquired instruction is a decision instruction. In cases in which a negative determination is made at step S1106, the processing of FIG. 11 transitions to step S1110.

At step 1110, the model generation section 174 sets the eyeball model candidate specified in the selection instruction as the eyeball model candidate to be emphatically displayed by the selection frame 76. The processing of FIG. 11 then returns to step S1102, and the eye axial length display region 72 and the eyeball model candidate display region 74 are again displayed on the display screen of the display 156 of the image viewer 150. The normal type model A selected at the start timing of the sub-routine is thus changed to the selected eyeball model candidate when this is performed. For example, when the spindle type model D has been specified in the selection instruction, the spindle type model D is emphatically displayed in the eyeball model candidate display region 74, and the outline of the spindle type model D and the three eye axial lengths D1, D2, D3 within the outline are displayed in the eye axial length display region 72.

In cases in which an affirmative determination is made at step S1106, the processing of FIG. 11 transitions to step S1108. At step S1108, the model generation section 174 records the one eyeball model candidate selected by the user as a three-dimensional eyeball model of the subject eye 12 in the secondary storage device 154 of the image viewer 150. The model generation section 174 then ends the eyeball model generation sub-routine (RETURN in FIG. 11).

Note that for ease of explanation, in the above explanation one of the eyeball model candidates (for example the normal type model A) is selected as the eyeball model candidate selected at the start timing of the sub-routine in FIG. 11 (namely, at step S1102, the normal type model A is emphatically displayed by the selection frame 76 in the eyeball model candidate display region 74, and its outline is displayed in the eye axial length display region 72). However, the model generation section 174 may predict an eyeball model candidate corresponding to the outline thought to be most suitable based on the eye axial lengths D1, D2, D3 and the value of the angle θ included in the eye axial length data, and set the predicted eyeball model candidate at the start timing of the sub-routine in FIG. 11. In such cases, the model generation section 174 may make a prediction using machine learning. Alternatively, the model generation section 174 may use personal information regarding the subject included in the eye axial length data, such as gender, age, race, and/or medical history, to predict an appropriate eyeball model candidate. Note that the personal information regarding the subject, such as gender, age, race, and/or medical history, is an example of patient information of the present disclosure.

In the above explanation, the eye axial lengths D1, D2, D3 are utilized as shape information regarding the subject eye 12 to assist a decision regarding the eyeball model by the user. However, the shape information regarding the subject eye is not limited to plural eye axial lengths. It is sufficient that the shape information be a quantity representing the shape of the subject eye 12 that is measurable by the eye axial length measurement device 120, and be capable of assisting the user in deciding which out of the five eyeball model candidates is appropriate as the eyeball model for the subject eye 12.

B: Position Determination

In FIG. 10, the processing of step S1008 onward is executed by the CPU 162 of the image viewer 150 functioning as the image generation section 176 and the image transmission section 179.

At step S1008 in FIG. 10, the image generation section 176 performs position determination. The position determination of the present disclosure refers to determining a correspondence relationship between plural points in the two-dimensional fundus image and positions in the three-dimensional eyeball model.

The position determination process of the first exemplary embodiment is illustrated in FIG. 15 as a sub-routine. FIG. 15 is a sub-routine illustrating an example of the processing program executed by the CPU 162 of the image viewer 150 when serving as the image generation section 176.

At step S1502, the image generation section 176 reads the two-dimensional fundus image data recorded in the secondary storage device 154 at the earlier step S1004 in FIG. 10. As an example, the image generation section 176 specifies three pixels A1, A2, A3 in the two-dimensional fundus image. The number of individual specified pixels is not limited to three, and should be an appropriate number to execute position determination.

At step S1504, the image generation section 176 acquires three pairs of angles ($\varphi_X$, $\varphi_Y$) corresponding to the three specified pixels A1, A2, A3 from the secondary storage device 154.

At step S1506, the image generation section 176 reads the three-dimensional eyeball model recorded in the secondary storage device 154 at the earlier step S1108 in FIG. 11. The image generation section 176 then computes three positions B1, B2, B3 corresponding to the three pairs of angles ($\varphi_X$, $\varphi_Y$) on the retinal surface of the three-dimensional eyeball model. Note that B1, B2, B3 represent reflection positions of incident light at the retinal surface of the three-dimensional eyeball model for hypothetical incident light from the angles ($\varphi_X$, $\varphi_Y$) toward the pupil center point 27 of the three-dimensional eyeball model.

At step S1508, the image generation section 176 computes position information based on the pixels A1, A2, A3 in the two-dimensional fundus image and the positions B1, B2, B3 on the retinal surface of the three-dimensional eyeball model. Since the pixels A1, A2, A3 in the two-dimensional fundus image correspond to three points in the imageable region 12A of the subject eye 12, performing positional alignment of the two-dimensional fundus image against the retinal surface of the three-dimensional eyeball model such that the pixels A1, A2, A3 match the respective positions B1, B2, B3 enables the correspondence relationship between the two-dimensional fundus image and the three-dimensional eyeball model to be determined. The position information of the first exemplary embodiment includes sufficient information to perform this position alignment.

At step S1510, the image generation section 176 records the generated position information in the secondary storage device 154 of the image viewer 150. The image generation section 176 then ends the position determination sub-routine (RETURN in FIG. 15).

C: Three-Dimensional Fundus Image Creation and Display

At the timing at which step S1008 in FIG. 10 ends, the two-dimensional fundus image data acquired at step S1004, the three-dimensional eyeball model generated at step S1006, and the position information generated at step S1008 are recorded for the subject eye 12 in the secondary storage device 154 of the image viewer 150.

At step S1010, the image generation section 176 reads the two-dimensional fundus image data, the three-dimensional eyeball model, and the position information from the secondary storage device 154 of the image viewer 150, performs image processing to generate a three-dimensional fundus image of the subject eye 12, and records this in the secondary storage device 154. Specifically, after determining the positions on the three-dimensional eyeball model of the plural points in the two-dimensional fundus image based on the position information, image processing is performed to wrap the two-dimensional fundus image onto the three-dimensional eyeball model, thereby generating a three-dimensional fundus image of the subject eye 12. An anterior segment region and eyeball regions that are not fully covered by the two-dimensional image may be patched using a predetermined image.

At the next step S1012, the image generation section 176 outputs an image signal to display a fundus image display screen 80 including the three-dimensional fundus image on the display screen of the display 156 of the image viewer 150. The display 156 displays the fundus image display screen 80 based on the image signal output by the CPU 162. The fundus image display screen 80 may display the two-dimensional fundus image at the same time.

Figure 16:
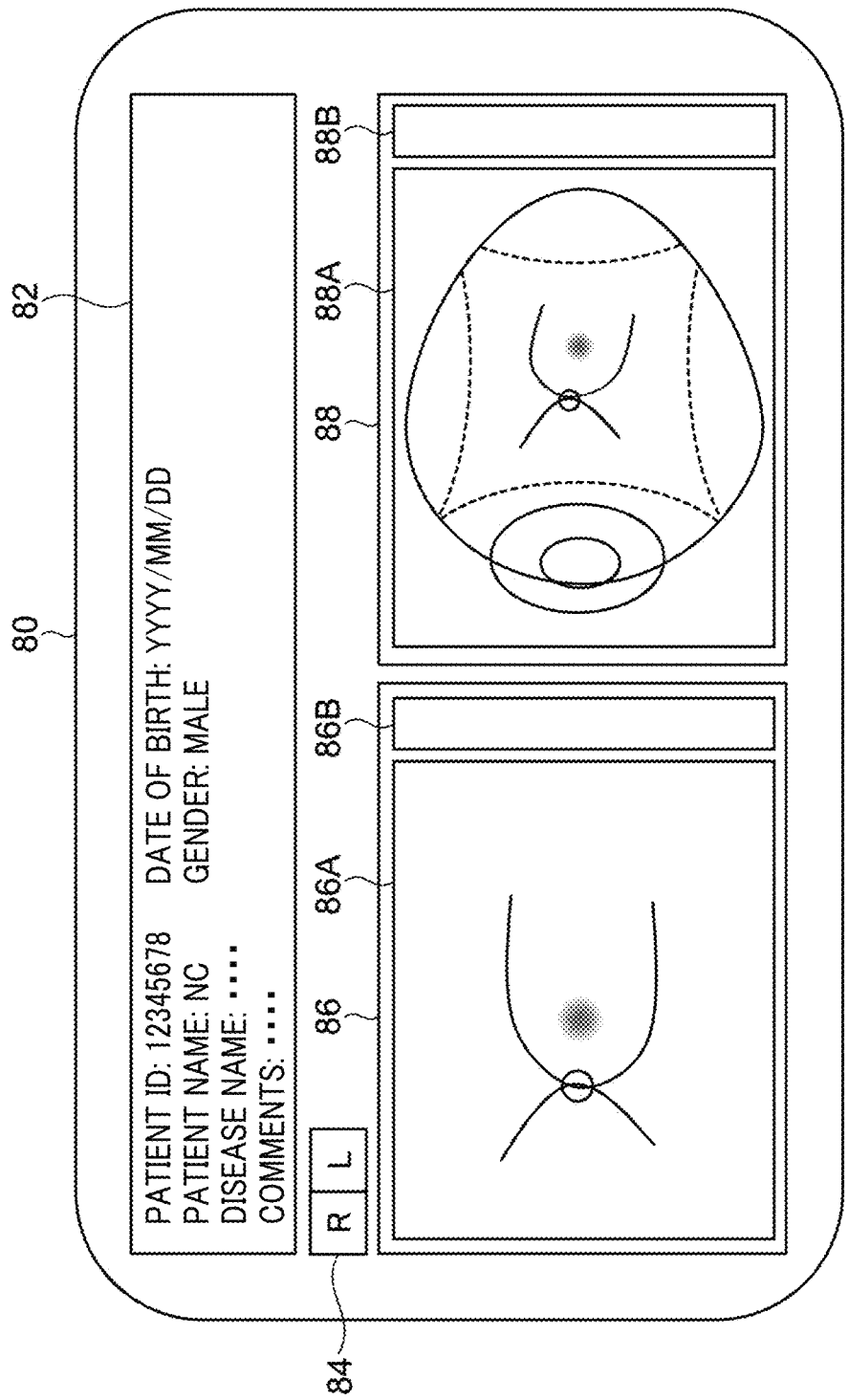
FIG. 16 is a diagram illustrating an example of a fundus image display screen according to the first exemplary embodiment.

FIG. 16 illustrates an example of the fundus image display screen 80. The fundus image display screen 80 in FIG. 16 includes: a subject information display region 82; a two-dimensional image display region 86 including a right eye/left eye switchover button 84, a two-dimensional fundus image display region 86A, and a first tool button 86B; and a three-dimensional image display region 88 including a three-dimensional fundus image display region 88A and a second tool button 88B.

The subject information display region 82 displays information identifying the subject, such as the subject ID. As an example, this information includes the date of birth, name, gender, disease name, and any comments by an ophthalmologist serving as an example of a user.

The switchover button 84 is a button for switching the subject eye 12 displayed on the fundus image display screen 80 between the right eye and left eye of the subject. In the interest of convenience, in the first exemplary embodiment the subject eye 12 is the left eye of the subject as previously described, and so further explanation regarding the switchover button 84 is omitted.

The two-dimensional fundus image of the subject eye 12 imaged by the ophthalmic imaging device 110 is displayed in the two-dimensional fundus image display region 86A based on the two-dimensional fundus image data recorded in the secondary storage device 154 of the image viewer 150. The first tool button 86B is a button for changing the size, adjusting the color, and so on of the display in the two-dimensional fundus image display region 86A.

The three-dimensional fundus image of the subject eye 12 generated at step S1010 and recorded in the secondary storage device 154 of the image viewer 150 is displayed in the three-dimensional fundus image display region 88A. The second tool button 88B is a button for changing the size, adjusting the color, and so on of the display in the three-dimensional fundus image display region 88A.

As described above, the two-dimensional fundus image of the subject eye 12 imaged by the ophthalmic imaging device 110 and the three-dimensional fundus image of this two-dimensional fundus image wrapped onto the three-dimensional eyeball model are respectively displayed in the two-dimensional fundus image display region 86A and the three-dimensional fundus image display region 88A in FIG. 16. The ophthalmologist who is the user is able to compare and observe these two images by viewing the respective display regions on the display screen of the display 156 of the image viewer 150 at step S1012. The ophthalmologist who is the user is then able to input an observation result and a diagnosis result into the comments field of the subject information display region 82. For example, the user may input the disease name and/or symptoms of the subject eye 12 as deduced as a result of fundus image observation into the comments field.

When a processing end instruction is input to the image viewer 150 by user operation of the mouse 155M or the keyboard 155K, processing transitions to step S1014. At step S1014, the image transmission section 179 associates the three-dimensional fundus image data for the subject eye 12 generated at step S1010 with the information identifying the subject displayed in the subject information display region, and transmits this to the image management server 140. The CPU 162 of the image viewer 150 thereby ends execution of the processing program illustrated in FIG. 10 (END in FIG. 10).

On receiving data from the image viewer 150, the control section of the image management server 140 records the received data in the secondary storage section of the image management server 140.

Figure 17:
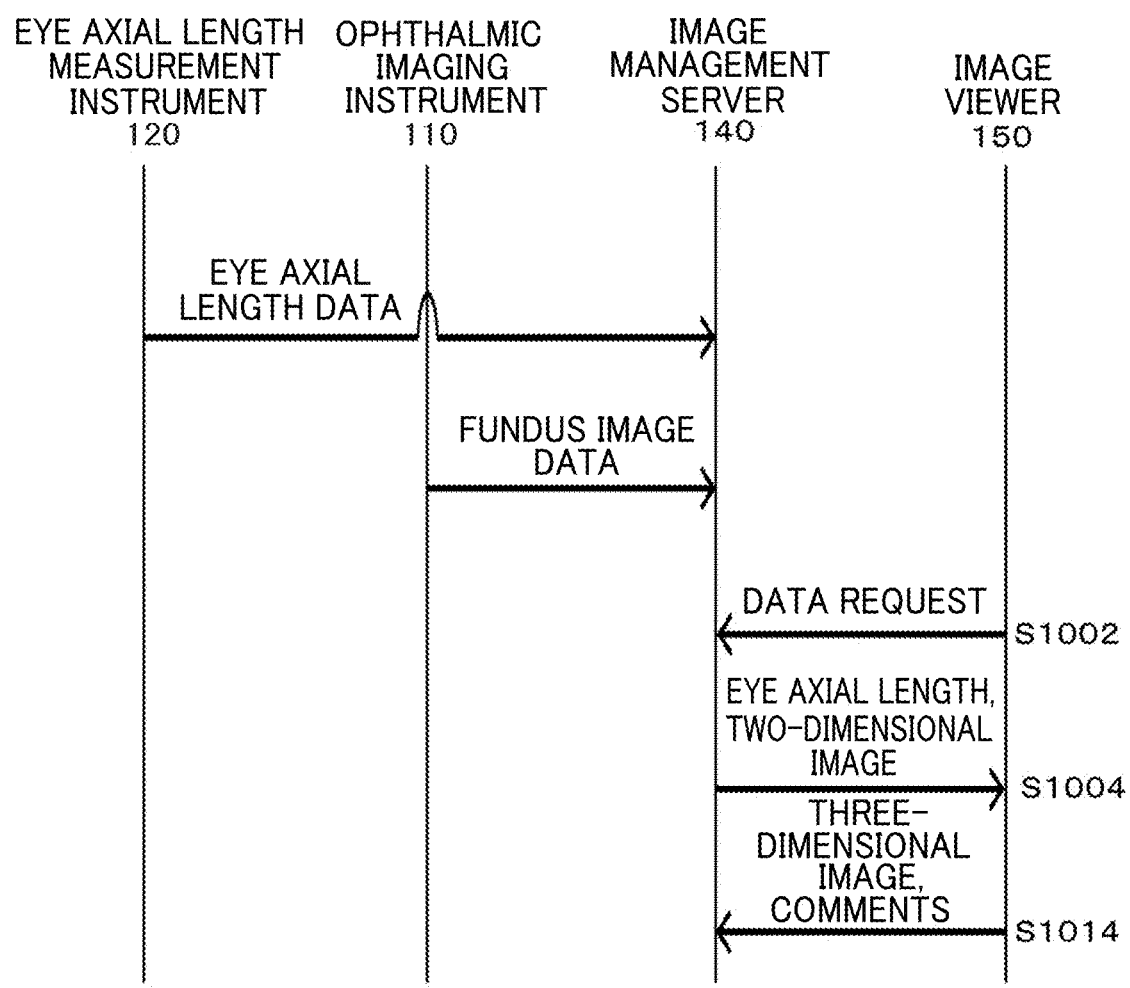
FIG. 17 is a sequence diagram illustrating exchange of data between various devices according to the first exemplary embodiment.

FIG. 17 is a sequencing diagram illustrating exchange of information between the ophthalmic imaging device 110, the eye axial length measurement device 120, the image management server 140, and the image viewer 150 relating to the first exemplary embodiment of the present disclosure as described above. Each step illustrated in FIG. 17 corresponds to a step in FIG. 10.

In the first exemplary embodiment of the present disclosure, a three-dimensional eyeball model that is appropriate for the subject eye can be easily generated by measuring a small number of eye axial lengths of the subject eye, performing suitable combination with predetermined eyeball model candidates and effective display thereof, and prompting the user to make a selection. Furthermore, a three-dimensional fundus image can be generated and displayed using the generated three-dimensional eyeball model.

Moreover, an OCT image display region to display an OCT tomographic image or an OCT three-dimensional image obtained by the OCT unit of the ophthalmic imaging device 110 may be provided in the fundus image display screen 80.

Modified Example of First Exemplary Embodiment: Time-Series Observation

As a modified example of the first exemplary embodiment of the present disclosure, the fundus image display system 100 according to the first exemplary embodiment may be utilized for time-series observation of a designated site of the fundus. Explanation follows regarding only points that differ from the first exemplary embodiment.

In this modified example, the designated site of the subject eye 12 is imaged by the ophthalmic imaging device 110 plural times with a predetermined interval therebetween to create plural two-dimensional fundus images. Herein, the plural times correspond to two times as an example.

First, all the processing according to the first exemplary embodiment is executed for the subject eye 12 of the subject (a first round of processing). After a fixed interval (such as three months) has elapsed, all the processing according to the first exemplary embodiment is again executed for the same subject eye 12 (a second round of processing). The processing itself is the same as that in the first exemplary embodiment each time. It should be noted that the site of the fundus imaged by the ophthalmic imaging device 110 and recorded in the image management server as fundus image data is the same site during both the first round and the second round.

Moreover, at the start timing of the sub-routine in FIG. 11 during the second round of processing, the eyeball model decided on at step S1006 in FIG. 10 has already been set during the first round of processing. This corresponds to the eyeball model utilized during the first round of processing being set as a primary candidate for the eyeball model during the second round of processing.

Suppose for example that the nose-side protrusion type model B is decided on as the eyeball model of the subject eye 12 during the first round of processing. In such a case, when the eyeball model generation sub-routine starts during the second round of processing, display on the display screen of the display 156 of the image viewer 150 at step S1102 is performed in the following manner. Of the five eyeball model candidates in the eyeball model candidate display region 74, the nose-side protrusion type model B (namely, the model utilized during the first round of processing) is emphatically displayed by the selection frame 76. Moreover, the outline of the nose-side protrusion type model B and the three eye axial lengths D1, D2, D3 within the outline are displayed in the eye axial length display region 72.

Suppose that at step S1108 in FIG. 11 during the second round of processing, a different model candidate to the model utilized during the first round of processing (the nose-side protrusion type model B in the above-described example) were to be recorded as the eyeball model. This signifies that the eyeball shape of the subject eye 12 has changed during the interval between the first round of processing and the second round of processing. The user is able to deduce from this fact that some kind of disease has developed in the subject eye 12. In such a case, the change in the eyeball shape of the subject eye 12 may be assessed by MRI using a non-illustrated MRI device, and the result thereof may be recorded in the secondary storage device 154 of the image viewer 150.

Alternatively, suppose that the two-dimensional fundus image imaged by the ophthalmic imaging device 110 during the first round of processing includes a lesion site. In such a case, the CPU 162 of the image viewer 150 may compute a change in the surface area of the lesion site between the three-dimensional fundus image obtained during the second round of processing and the three-dimensional fundus image obtained during the first round of processing, and record this in the secondary storage device 154.

In this modified example of the first exemplary embodiment, change information serving as data indicating an assessment result of change in the eyeball shape, and/or a change in the surface area of a lesion site is obtained during the second round of processing. At step S1014 in FIG. 10 during the second round of processing, after adding the change information to the information identifying the subject, the image transmission section 179 may associate the change information with the three-dimensional fundus image data for the subject eye 12 and transmit this to the image management server 140. The processing program executed by the CPU 162 of the image viewer 150 is then ended (END in FIG. 10 during the second round of processing).

Figure 18:
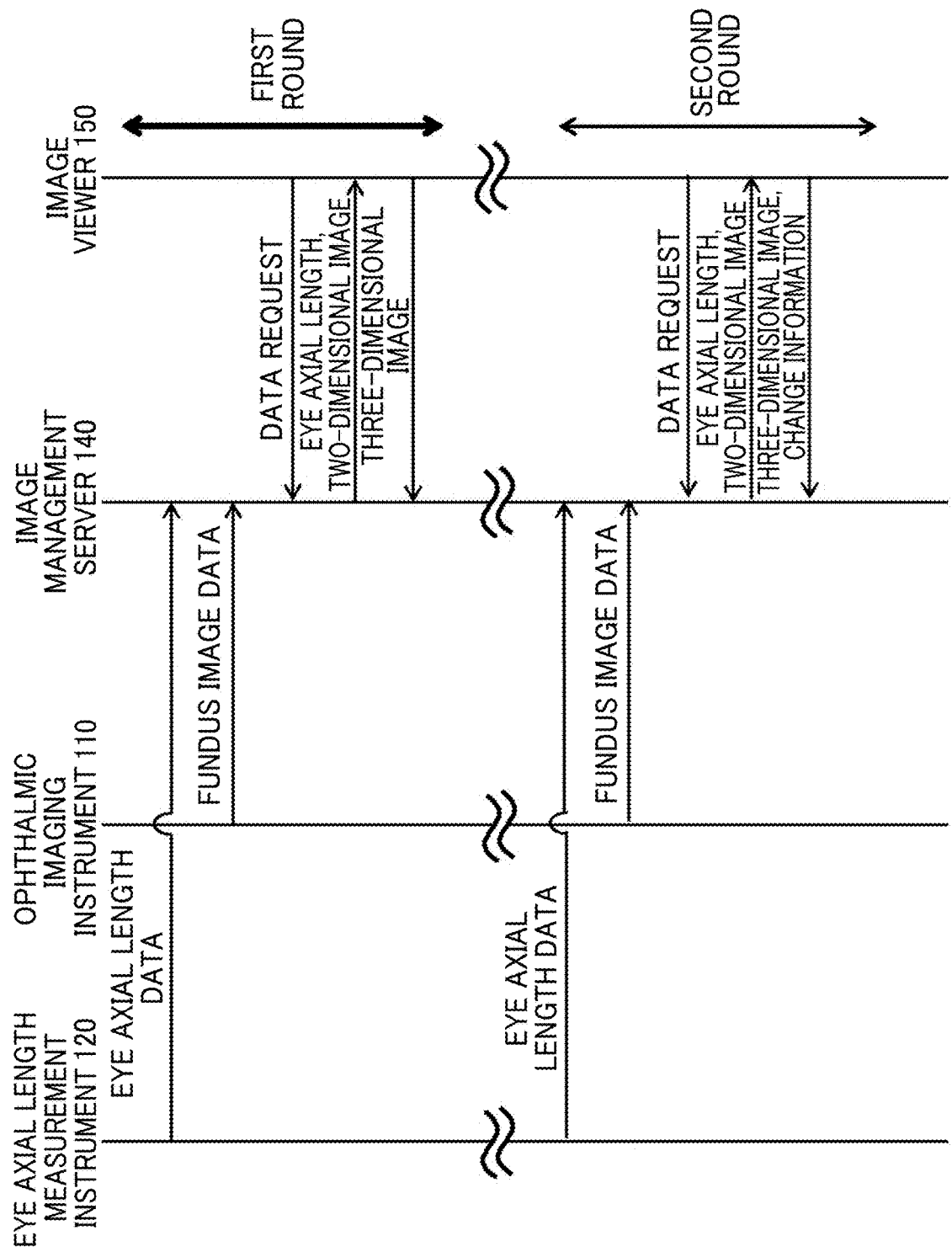
FIG. 18 is a sequence diagram illustrating exchange of data between various devices according to a modified example of the first exemplary embodiment.

FIG. 18 is a sequencing diagram illustrating exchange of information between the ophthalmic imaging device 110, the eye axial length measurement device 120, the image management server 140, and the image viewer 150 relating to the modified example of the first exemplary embodiment of the present disclosure described above.

Figure 19:
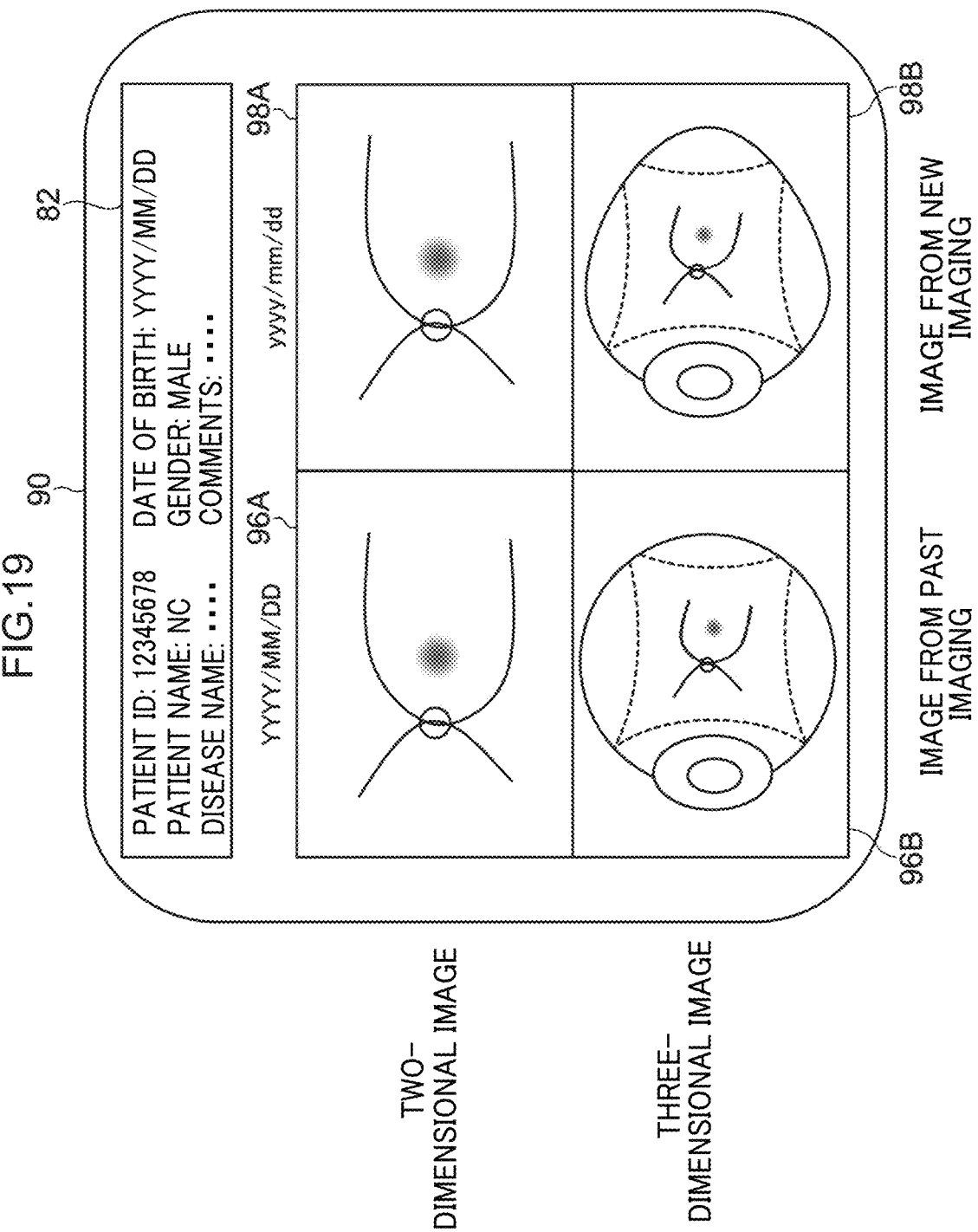
FIG. 19 is a diagram illustrating an example of a fundus image comparison display screen according to a modified example of first exemplary embodiment.

At step S1012 in FIG. 10 during the second round of processing, the image generation section 176 may output an image signal to display a fundus image comparison display screen 90 illustrated in FIG. 19 on the display screen of the display 156 of the image viewer 150 instead of the fundus image display screen 80 illustrated in FIG. 16.

The fundus image comparison display screen 90 in FIG. 19 includes the subject information display region 82, a past two-dimensional fundus image display region 96A, a past three-dimensional fundus image display region 96B, a new two-dimensional fundus image display region 98A, and a new three-dimensional fundus image display region 98B. The two-dimensional fundus image and the three-dimensional fundus image from the first round of processing are respectively displayed in the past two-dimensional fundus image display region 96A and the past three-dimensional fundus image display region 96B. The two-dimensional fundus image and the three-dimensional fundus image from the second round of processing are respectively displayed in the new two-dimensional fundus image display region 98A and the new three-dimensional fundus image display region 98B.

Although not illustrated in FIG. 19, the fundus image comparison display screen 90 may include tool buttons that correspond to the first tool button 86B and the second tool button 88B illustrated in FIG. 16 for changing the size, adjusting the color, and so on of the fundus image display.

It should be noted that in the example illustrated in FIG. 19, the eyeball model generated during the first round of processing is the normal type model A, whereas the eyeball model generated during the second round of processing is the spindle type model D. In such a case, the eyeball shape of the subject eye 12 has changed during the interval between the first round and the second round, and so it may be deduced that some kind of disease has developed in the subject eye 12.

Besides time-series observation using past and new two-dimensional fundus images imaged at two different points in time, time-series observation may also be performed using two or more fundus images imaged during patient hospital visits. In such cases, two or more display regions to display past two-dimensional/three-dimensional fundus images, and one display region to display a newly obtained two-dimensional/three-dimensional fundus image may be provided on the fundus image comparison display screen 90.

The past three-dimensional fundus image display region 96B and the new three-dimensional fundus image display region 98B may be display regions with mutually different sizes instead of display regions with the same size. There is no limitation to the above-described examples, and various modes of display screen may be applied within the design scope.

Moreover, an OCT image display region to display an OTC tomographic image or an OCT three-dimensional image obtained by the OCT unit of the ophthalmic imaging device 110 may be provided on the fundus image comparison display screen 90.

The modified example of the first exemplary embodiment of the present disclosure enables time-series observation of the subject eye to be effectively performed.

Second Exemplary Embodiment

Explanation follows regarding a second exemplary embodiment of the present disclosure. Note that portions with similar configuration to that of the first exemplary embodiment are allocated with the same reference numerals, and explanation thereof is omitted.

System Overview

Figure 20:
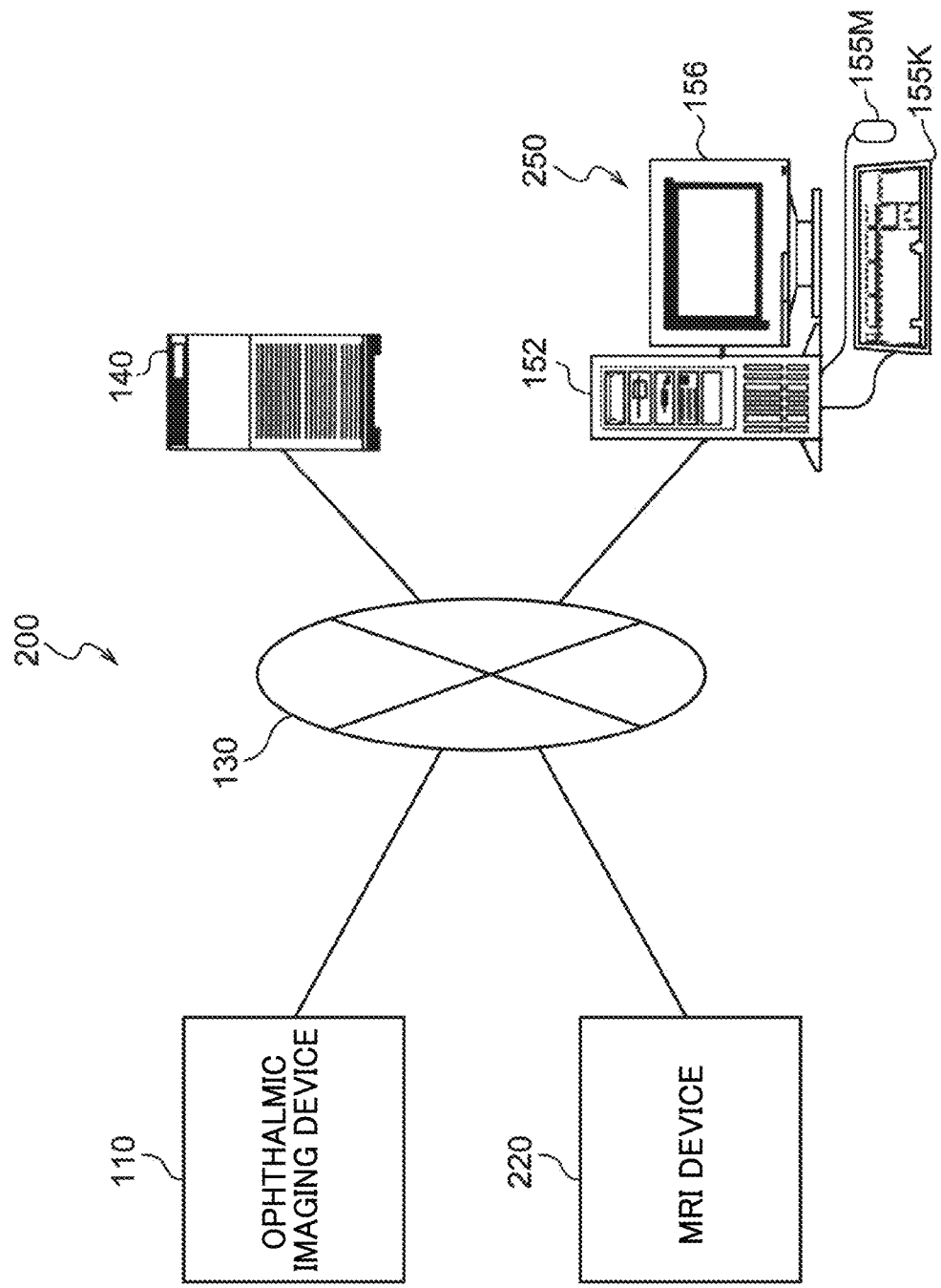
FIG. 20 is a diagram illustrating an example of a schematic configuration of a fundus image display system according to a second exemplary embodiment of the present disclosure.

Explanation follows regarding configuration of a fundus image display system 200 according to the second exemplary embodiment, with reference to FIG. 20. The fundus image display system 200 includes an MRI device 220 instead of the eye axial length measurement device 120. The fundus image display system 200 also includes an image viewer 250 instead of the image viewer 150 of the first exemplary embodiment. The image viewer 250 includes a CPU 262 instead of the CPU 162. Although the example given here employs a single CPU, the technology disclosed herein is not limited thereto, and plural CPUs may be applied. Note that the image viewer 250 is an example of a three-dimensional fundus image generation device of the present disclosure.

Three-Dimensional Fundus Image Generation and Recording Process

Detailed explanation follows regarding generation and recording of a three-dimensional fundus image in the second exemplary embodiment.

Imaging of Fundus Image

This is similar to in the first exemplary embodiment, and so explanation thereof is omitted. However, due to a relationship with position determination, described later, a two-dimensional fundus image imaged by the ophthalmic imaging device 110 of the second exemplary embodiment needs to include two biological feature points.

MRI Imaging

The fundus image display system 200 performs three-dimensional MRI imaging of the subject eye 12 using the MRI device 220 instead of the eye axial length measurement by the eye axial length measurement device 120. Thus, detailed information is obtained regarding the shape of the subject eye 12, rather than simply eye axial lengths.

A non-illustrated control device of the MRI device 220 transmits the subject ID and MRI shape data regarding the shape of the subject eye 12 acquired using three-dimensional MRI imaging to the image management server 140 via the network 130. The non-illustrated control device of the image management server 140 associates the received MRI shape data with the subject ID relating to the subject eye 12, and records this in a non-illustrated secondary storage device.

Processing Executed by Image Viewer 250

In the second exemplary embodiment, a three-dimensional eyeball model is decided on by the CPU 262 of the image viewer 250 functioning as a model generation section 274, based on the MRI shape data relating to the shape of the subject eye 12 acquired by the MRI device 220. The CPU 262 of the image viewer 250 then wraps the two-dimensional fundus image imaged by the ophthalmic imaging device 110 onto the three-dimensional eyeball model to generate a three-dimensional fundus image.

Figure 21:
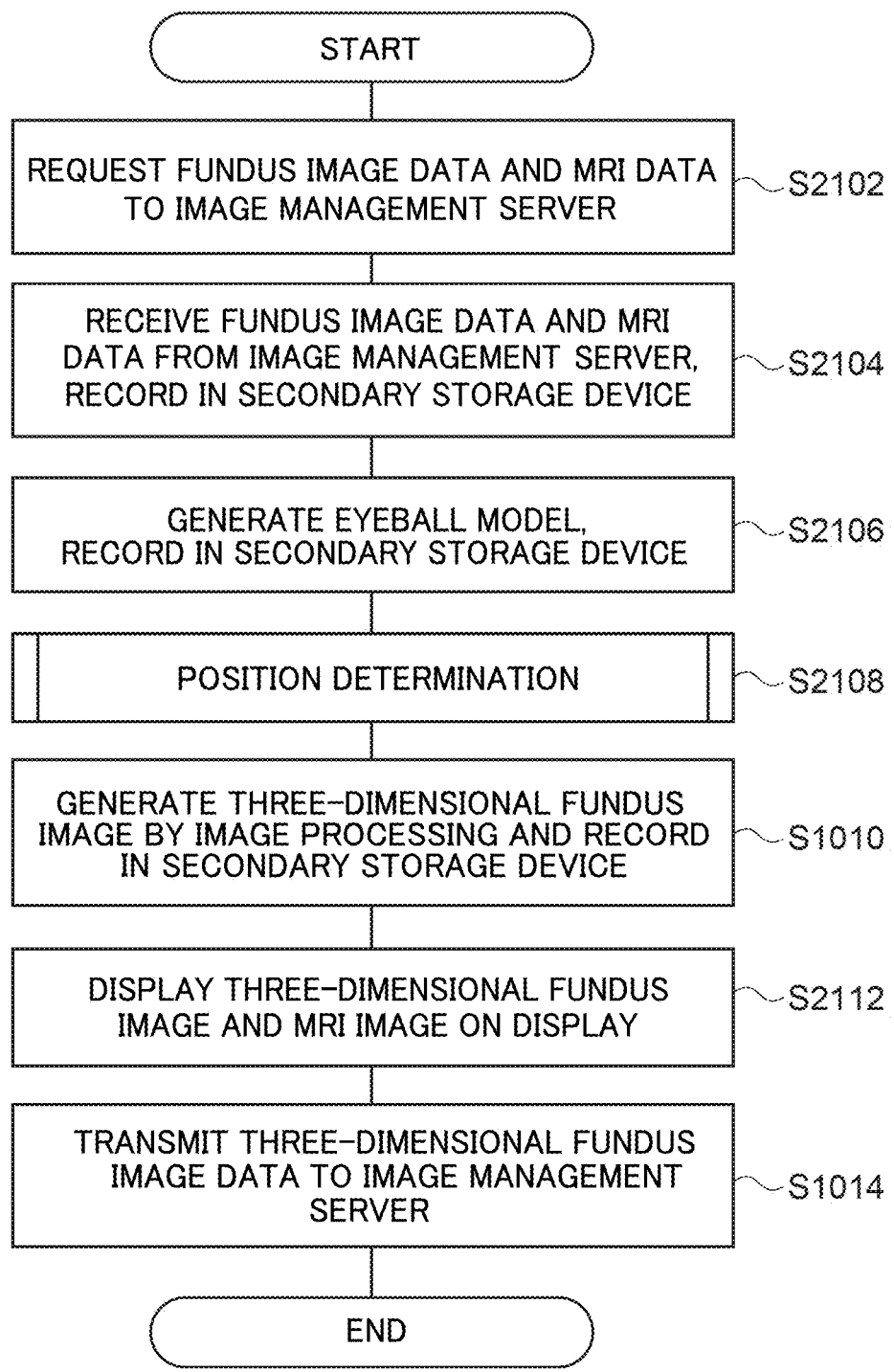
FIG. 21 is a flowchart illustrating an example of a program executed by a CPU of an image viewer according to the second exemplary embodiment.
Figure 22:
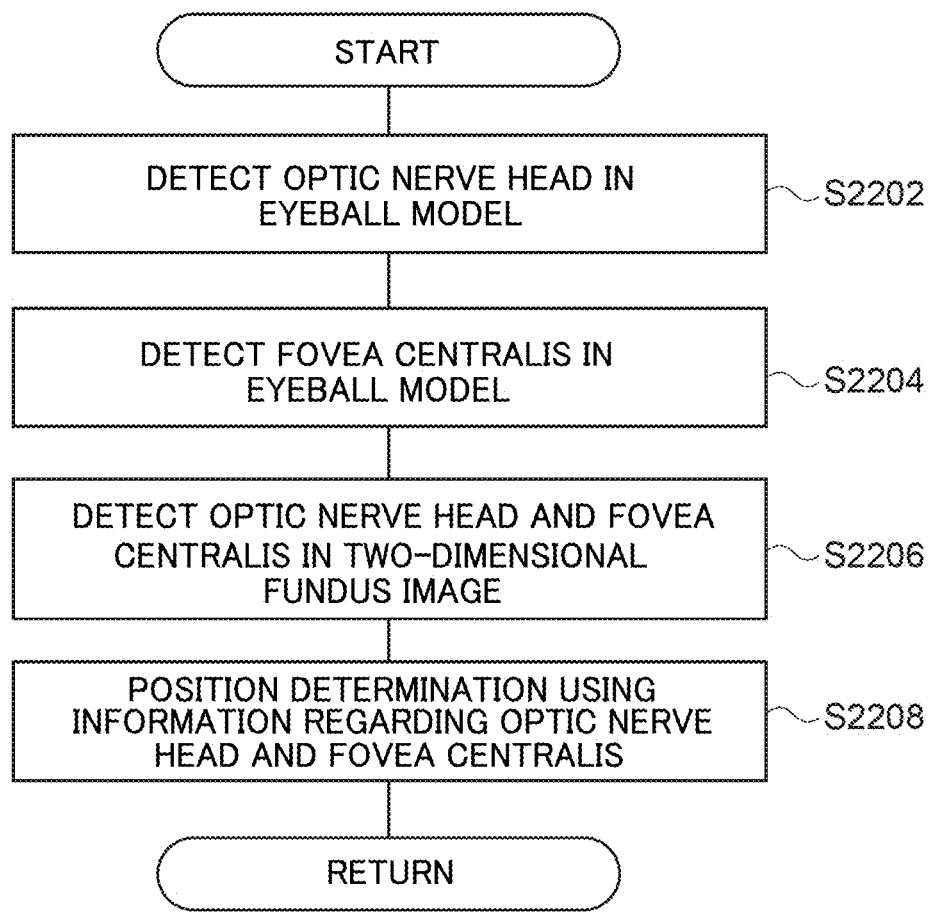
FIG. 22 is a flowchart illustrating contents of a position determination sub-routine according to the second exemplary embodiment.

FIG. 21 and FIG. 22 are flowcharts illustrating an example of a processing program to perform three-dimensional fundus image display in the second exemplary embodiment. FIG. 21 and FIG. 22 illustrate an example of a processing program executed by the image viewer 250.

Specifically, the processing program executed by the image viewer 250 is executed by the CPU 262 of the image viewer 250 functioning as a data acquisition section 272, the model generation section 274, an image generation section 276, and an image transmission section 279.

Here, it is assumed that imaging of the two-dimensional fundus image by the ophthalmic imaging device 110 and three-dimensional MRI imaging by the MRI device 220 for the subject eye 12 of the subject have already ended, and that the two-dimensional fundus image data and the MRI shape data are stored in the non-illustrated secondary storage device of the image management server 140. A user wishing to generate a three-dimensional fundus image inputs this intention to the image viewer 250 by operating the mouse 155M or the keyboard 155K. This starts execution of the processing program illustrated in FIG. 21 and FIG. 22 by the image viewer 250, and starts a processing process to perform three-dimensional fundus image display according to the second exemplary embodiment. FIG. 21 is a flowchart illustrating the overall processing process.

A: Eyeball Model Generation

The data acquisition section 272 executes the processing at steps S2102, S2104 in FIG. 21. The model generation section 274 executes the processing at step S2106 in FIG. 21.

Steps S2102 and S2104 only differ from steps S1002 and S1004 in FIG. 10 of the first exemplary embodiment in that the exchanged data includes MRI shape data instead of eye axial length data. Detailed explanation thereof is therefore omitted.

Processing then transitions to step S2106. The following processing is executed by the model generation section 274.

At step S2106, the model generation section 274 generates a three-dimensional eyeball model of the subject eye 12 using the MRI shape data for the subject eye 12 by employing existing three-dimensional MRI technology, and records this in the secondary storage device 154 of the image viewer 250. Thus, the eyeball model generation of the second exemplary embodiment does not include the processes of the first exemplary embodiment in which the five models are provisionally set based on medical knowledge, and the user makes a selection and decision thereupon.

B: Position Determination

In FIG. 21, processing from step S2108 onward is executed by the CPU 262 of the image viewer 250 functioning as the image generation section 276 and the image transmission section 279.

At step S2108 in FIG. 21, the image generation section 276 performs position determination.

The position determination process in the second exemplary embodiment is illustrated in FIG. 22 as a sub-routine. FIG. 22 is a sub-routine illustrating an example of the processing program executed by the CPU 262 of the image viewer 250 when serving as the image generation section 276.

The position determination of the second exemplary embodiment is performed using the positions of two biological feature points on the fundus. Specifically, position determination is performed such that the positions of a first feature point and a second feature point in the three-dimensional eyeball model conform to the respective positions of the first feature point and the second feature point in the two-dimensional fundus image.

As an example, a fundus image in the vicinity of the center of the fundus is imaged by the ophthalmic imaging device 110 of the second exemplary embodiment. In such a case, the first feature point may be the fovea centralis, and the second feature point may be an optic nerve head position.

At step S2202, the image generation section 276 detects the optic nerve head position in the three-dimensional eyeball model. Detailed information regarding the shape of the subject eye 12 is included in the MRI shape data (acquired by the MRI device 220 and recorded in the secondary storage device 154 of the image viewer 250). Thus, a point where the eyeball and the optic nerve intersect at the posterior segment in the three-dimensional eyeball model is detected from the MRI shape data by using known three-dimensional MRI technology, and this point is identified as the optic nerve head position in the three-dimensional eyeball model.

At the next step S2204, the image generation section 276 detects the fovea centralis in the three-dimensional eyeball model. Detailed information regarding the shape of the subject eye 12 is included in the MRI shape data, and so the fovea centralis can be detected in the three-dimensional eyeball model from the MRI shape data by using known three-dimensional MRI technology.

Figure 23:
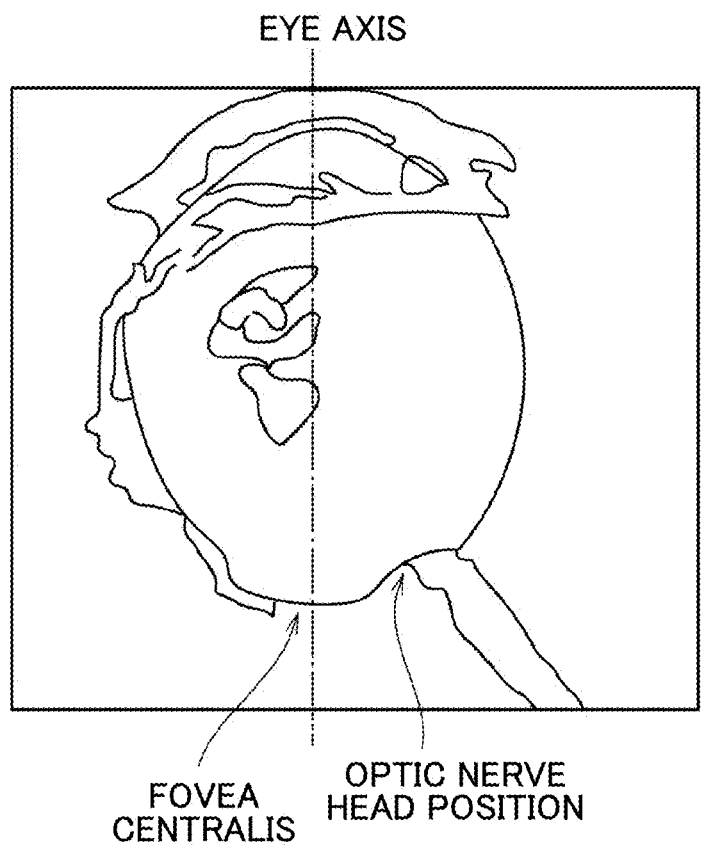
FIG. 23 is a diagram illustrating an example of feature point detection on an eyeball model according to the second exemplary embodiment.

FIG. 23 illustrates an example of detection of the optic nerve head position and the fovea centralis in the three-dimensional eyeball model. A point where an eye axis parallel to the Z axis and passing through the eyeball center O intersects the posterior segment is identified as the fovea centralis.

Next, at step S2206, the image generation section 276 detects the fovea centralis and the optic nerve head position in the two-dimensional planar image using known image processing technology.

Figure 24:
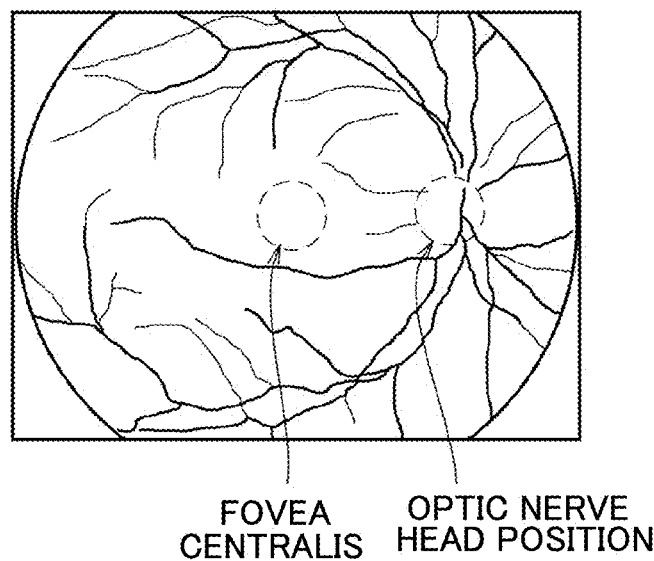
FIG. 24 is a diagram illustrating an example of feature point detection in a two-dimensional fundus image according to the second exemplary embodiment.

FIG. 24 illustrates an example of detection of the fovea centralis and the optic nerve head position in the two-dimensional planar image.

Note that the sequence of steps S2202, S2204, and S2206 is interchangeable.

At step S2208, the image generation section 276 performs position determination such that the fovea centralis and the optic nerve head position in the three-dimensional eyeball model respectively conform to the fovea centralis and the optic nerve head position in the two-dimensional fundus image. The image generation section 276 then ends the position determination sub-routine (RETURN in FIG. 22).

C: Three-Dimensional Fundus Image Creation and Display

The processing by the image generation section 276 transitions to step S1010 in FIG. 21. Steps S1010 and S1014 are similar to the processing of the first exemplary embodiment illustrated in FIG. 10, and so explanation thereof is omitted.

However, display on the display at step S2112 in FIG. 21 differs from the display in the first exemplary embodiment illustrated in FIG. 16, and so explanation follows regarding this point. FIG. 25 illustrates an example of a fundus image display screen 280 displayed on the display screen of the display 156 of the image viewer 250 based on an image signal generated by the image generation section 276 at step S2012.

The fundus image display screen 280 illustrated in FIG. 25 includes a two-dimensional fundus image display region 286, a three-dimensional fundus image display region 288, and an eyeball model display region 290. The fundus image display screen 280 of the second exemplary embodiment differs from the fundus image display screen 80 of the first exemplary embodiment illustrated in FIG. 16 in the respect that the three-dimensional eyeball model itself generated from the MRI shape data acquired by the MRI device 220 is displayed in the eyeball model display region 290.

In the above explanation, the two biological feature points in the position determination of the second exemplary embodiment are the fovea centralis and the optic nerve head. However, the biological feature points are not limited thereto, and any points may be applied as long as they are included in the fundus region imaged by the ophthalmic imaging device 110 and can be utilized for position determination.

In the second exemplary embodiment of the present disclosure, plural biological feature points on the fundus of the subject eye are utilized to perform appropriate position determination on an accurate three-dimensional eyeball model based on three-dimensional MRI imaging, after which image processing is performed to wrap the two-dimensional fundus image thereon, thereby enabling a three-dimensional fundus image to be obtained that more closely reflects reality.

The processing processes described in the above exemplary embodiments, namely, the processing process illustrated in FIG. 10, FIG. 11, FIG. 15, FIG. 21, and FIG. 22 (hereafter simply referred to as processing processes) are merely examples. Thus, obviously unnecessary steps may be omitted, new steps may be added, and the processing sequence may be changed within a range not departing from the spirit of the technology disclosed herein.

Moreover, in the above exemplary embodiments, examples have been given which a computer is utilized to implement the processing processes using a software configuration, however the technology disclosed herein is not limited thereto. For example, instead of a software configuration utilizing a computer, the processing processes may be executed by a hardware configuration alone, such as a field-programmable gate array (FPGA) or an application specific integrated circuit (ASIC). The processing processes may be executed by a combination of a software configuration and a hardware configuration.

An example of a hardware resource to execute the processing processes is a CPU, this being a general-purpose processor functioning as a hardware resource to execute the various types of processing by executing a program. Other examples of hardware resources include dedicated electric circuits, these being processors including a custom-designed circuit configuration such as an FPGA, a programmable logic device (PLD) or an ASIC. An electric circuit combining circuit elements such as semiconductor elements may be employed as the hardware structure of these processors. The hardware resources executing the various types of processing may be any one of the plural types of processor described above, or a combination of two or more of the same type or different types of processor.

The content of the above description and the content of the drawings are a detailed description of portions according to the technology disclosed herein, and are merely examples of the technology disclosed herein. For example, the above description regarding configuration, functionality, operation, and advantageous effects is description regarding examples of configuration, functionality, operation, and advantageous effects according to the technology disclosed herein. Thus, obviously unnecessary portions may be omitted, new elements may be added, or substitutions may be made to the content of the above description and content of the drawings within a range not departing from the spirit of the technology disclosed herein. Moreover, in order to avoid confusion and to facilitate understanding of portions according to the technology disclosed herein, description regarding common technical knowledge and the like that does not require particular explanation to enable implementation of the technology disclosed herein has been omitted from the content of the above description and the content of the drawings.

In the present specification, "A and/or B" is synonymous with "at least one out of A or B". Namely, "A and/or B" may refer to A alone, B alone, or to a combination of A and B. Moreover, in the present specification, a similar concept to "A and/or B" applies in cases in which three or more elements are linked by an expression including "and/or".

This disclosure claims priority over Japanese Patent Application No. 2017-199485 filed on Oct. 13, 2017 and the entire content thereof is incorporated by reference in the present specification. All cited documents, patent applications, and technical standards mentioned in the present specification are incorporated by reference in the present specification to the same extent as if each individual cited document, patent application, or technical standard was specifically and individually indicated to be incorporated by reference.

The invention claimed is:

1. An image processing method comprising:
   displaying an eyeball model selection screen for selecting one eyeball model from out of a plurality of eyeball models of different forms;
   selecting one eyeball model from out of the plurality of eyeball models;
   converting a two-dimensional fundus image of a subject eye so as to generate a three-dimensional fundus image based on a selected eyeball model and a position of imaging said two-dimensional fundus image; and
   displaying a fundus image display screen including the three-dimensional fundus image,
   wherein the selecting one eyeball model out of the plurality of eyeball models comprises selecting one eyeball model from out of the plurality of eyeball models based on:
      a distance, passing through a center of a pupil of the subject eye, from a first predetermined point on a cornea of the subject eye to a first point on a retina of the subject eye;
      a distance, passing through the center of the pupil of the subject eye, from a second predetermined point on the cornea of the subject eye to a second point on the retina;
      a distance, passing through the center of the pupil of the subject eye, from a third predetermined point on the cornea of the subject eye to a third point on the retina;
      a first angle formed by a line connecting the center of the pupil of the subject eye and the first point, and a reference line, which connects an eyeball center of the subject eye and the center of the pupil;
      a second angle formed by a line connecting the center of the pupil and the second point, and the reference line; and
      a third angle formed by a line connecting the center of the pupil and the third point, and the reference line.

2. The image processing method of claim 1, wherein the eyeball model selection screen includes:
   an eye axial length display region configured to display an eye axial length of the subject eye; and
   an eyeball model display region configured to display the plurality of eyeball models.

3. The image processing method of claim 2, wherein a plurality of eye axial lengths measured at different fixation positions are displayed in the eye axial length display region.

4. The image processing method of claim 2, wherein:
   a graphic representing the plurality of eyeball models, text representing names of the plurality of eyeball models, or a combination of the graphic and the text, are displayed in the eyeball model display region.

5. The image processing method of claim 1, wherein the fundus image display screen includes:
   a two-dimensional fundus image display region configured to display the two-dimensional fundus image; and
   a three-dimensional fundus image display region configured to display the three-dimensional fundus image.

6. A non-transitory computer readable medium storing a program to cause a computer to execute processing including:
   displaying an eyeball model selection screen for selecting one eyeball model from out of a plurality of eyeball models of different forms;
   selecting one eyeball model from out of the plurality of eyeball models;
   converting a two-dimensional fundus image so as to generate a three-dimensional fundus image based on a selected eyeball model and a position of imaging said two-dimensional fundus image; and
   displaying a fundus image display screen including the three-dimensional fundus image, wherein the selecting one eyeball model out of the plurality of eyeball models comprises selecting one eyeball model from out of the plurality of eyeball models based on:
- a distance, passing through a center of a pupil of the subject eye, from a first predetermined point on a cornea of the subject eye to a first point on a retina of the subject eye;
- a distance, passing through the center of the pupil of the subject eye, from a second predetermined point on the cornea of the subject eye to a second point on the retina;
- a distance, passing through the center of the pupil of the subject eye, from a third predetermined point on the cornea of the subject eye to a third point on the retina;
- a first angle formed by a line connecting the center of the pupil of the subject eye and the first point, and a reference line, which connects an eyeball center of the subject eye and the center of the pupil;
- a second angle formed by a line connecting the center of the pupil and the second point, and the reference line; and
- a third angle formed by a line connecting the center of the pupil and the third point, and the reference line.

7. A non-transitory computer readable medium storing a program to cause a computer to execute processing including:
- generating an eyeball model selection screen for selecting one eyeball model from out of a plurality of eyeball models of different forms;
- selecting one eyeball model from out of the plurality of eyeball models;
- converting a two-dimensional fundus image so as to generate a three-dimensional fundus image based on a selected eyeball model and a position of imaging said two-dimensional fundus image;
- generating a fundus image display screen including the three-dimensional fundus image; and
- outputting an image signal corresponding to the eyeball model selection screen or the fundus image display screen,
wherein the comprises selecting one eyeball model from out of the plurality of eyeball models is based on:
- a distance, passing through a center of a pupil of the subject eye, from a first predetermined point on a cornea of the subject eye to a first point on a retina of the subject eye;
- a distance, passing through the center of the pupil of the subject eye, from a second predetermined point on the cornea of the subject eye to a second point on the retina;
- a distance, passing through the center of the pupil of the subject eye, from a third predetermined point on the cornea of the subject eye to a third point on the retina;
- a first angle formed by a line connecting the center of the pupil of the subject eye and the first point, and a reference line, which connects an eyeball center of the subject eye and the center of the pupil;
- a second angle formed by a line connecting the center of the pupil and the second point, and the reference line; and
- a third angle formed by a line connecting the center of the pupil and the third point, and the reference line.

8. An ophthalmic system comprising:
an ophthalmic imaging device; and
an image processing device configured to execute processing including
- displaying an eyeball model selection screen for selecting one eyeball model from out of a plurality of eyeball models of different forms,
- selecting one eyeball model from out of the plurality of eyeball models;
- converting a two-dimensional fundus image obtained by imaging using the ophthalmic imaging device so as to generate a three-dimensional fundus image based on a selected eyeball model and a position of imaging said two-dimensional fundus image, and
- displaying a fundus image display screen including the three-dimensional fundus image,
wherein the selecting one eyeball model out of the plurality of eyeball models comprises selecting one eyeball model from out of the plurality of eyeball models based on:
- a distance, passing through a center of a pupil of the subject eye, from a first predetermined point on a cornea of the subject eye to a first point on a retina of the subject eye;
- a distance, passing through the center of the pupil of the subject eye, from a second predetermined point on the cornea of the subject eye to a second point on the retina;
- a distance, passing through the center of the pupil of the subject eye, from a third predetermined point on the cornea of the subject eye to a third point on the retina;
- a first angle formed by a line connecting the center of the pupil of the subject eye and the first point, and a reference line, which connects an eyeball center of the subject eye and the center of the pupil;
- a second angle formed by a line connecting the center of the pupil and the second point, and the reference line; and
- a third angle formed by a line connecting the center of the pupil and the third point, and the reference line.

* * * * *